US010183047B2

(12) United States Patent
Kalidindi

(10) Patent No.: US 10,183,047 B2
(45) Date of Patent: Jan. 22, 2019

(54) **CHROMIUM-CONTAINING COMPOSITIONS IN COMBINATION WITH *PHYLLANTHUS EMBLICA* AND SHILAJIT HAVING SYNERGISTIC EFFECTS FOR IMPROVING ENDOTHELIAL FUNCTION AND CARDIOVASCULAR HEALTH**

(71) Applicant: Natreon, Inc., New Brunswick, NJ (US)

(72) Inventor: Sanyasi R. Kalidindi, Monroe, NJ (US)

(73) Assignee: Natreon, Inc., New Brunswick, NJ (US)

( * ) Notice: Subject to any disclaimer, the term of this patent is extended or adjusted under 35 U.S.C. 154(b) by 0 days.

(21) Appl. No.: 14/947,987

(22) Filed: Nov. 20, 2015

(65) Prior Publication Data

US 2016/0074452 A1 Mar. 17, 2016

Related U.S. Application Data

(63) Continuation-in-part of application No. 14/718,613, filed on May 21, 2015, now abandoned.

(60) Provisional application No. 62/001,438, filed on May 21, 2014.

(51) Int. Cl.
| | |
|---|---|
| *A61K 36/185* | (2006.01) |
| *A61K 33/24* | (2006.01) |
| *A61K 35/04* | (2006.01) |
| *A61K 36/47* | (2006.01) |
| *A61K 31/194* | (2006.01) |
| *A61K 31/366* | (2006.01) |

(52) U.S. Cl.
CPC .......... *A61K 36/185* (2013.01); *A61K 31/194* (2013.01); *A61K 31/366* (2013.01); *A61K 33/24* (2013.01); *A61K 35/04* (2013.01); *A61K 36/47* (2013.01)

(58) Field of Classification Search
CPC .... A61K 31/194; A61K 31/366; A61K 35/04; A61K 36/185; A61K 36/47; A61K 33/24; A61K 2300/00
See application file for complete search history.

(56) References Cited

U.S. PATENT DOCUMENTS

| | | | | |
|---|---|---|---|---|
| 6,124,268 | A * | 9/2000 | Ghosal | A61K 8/498 424/401 |
| 6,440,436 | B1 | 8/2002 | Ghosal | |
| 6,869,612 | B2 | 3/2005 | Ghosal | |
| 7,250,181 | B2 | 7/2007 | Ghosal | |
| 8,062,677 | B2 | 11/2011 | Komorowski | |
| 8,962,576 | B2 | 2/2015 | Ghosal et al. | |
| 2005/0085454 | A1 * | 4/2005 | Ghosal | A61K 31/28 514/185 |
| 2005/0233942 | A1 * | 10/2005 | Ghosal | A61K 31/366 514/5.5 |
| 2005/0245434 | A1 | 11/2005 | Ghosal | |
| 2009/0155384 | A1 * | 6/2009 | Komorowski | A61K 47/48061 424/655 |
| 2013/0261068 | A1 | 10/2013 | Ghosal et al. | |
| 2013/0266676 | A1 | 10/2013 | Ghosal et al. | |
| 2014/0079729 | A1 | 3/2014 | Kalidindi | |
| 2014/0356466 | A1 | 12/2014 | Ghosal et al. | |

FOREIGN PATENT DOCUMENTS

| | | |
|---|---|---|
| WO | 2009/010992 A2 | 1/2009 |
| WO | 2011/139246 A1 | 11/2011 |

OTHER PUBLICATIONS

Usharani et al (2013). "Effects of Phyllanthus emblica extract on endothelial dysfunctional and biomarkers of oxidative stress in patients with type 2 diabetes mellitus: a randomized, double-blind, controlled study." Diabetes, Metabolic Syndrom and Obesity: Targets and Therapy, 6: 275-284.*
Saxena et al (2003). "Modulation of Oxidative and Antioxidative Status of Diabetes by Asphaltum Panjabinum." Diabetes Care, 26(8): 2469-2470.*
Hadi et al (2005). Vascular Health and Risk Management, 1(3): 183-198.*
Akhtar, et al., "Effect of Amla fruit (*Emblica officinalis* Gaertn.) on blood glucose and lipid profile of normal subjects and type 2 diabetic patients," Int. J. Food Sci. Nutr. (2011) 62(6): 609-616. Abstract Only.
Anila, et al., "Flavonoids from Emblica Officinalis and Mangifera indica-effectiveness for dyslipidemia," J. Ethnopharmacol. (2002) 79:81-7.
Bhattacharya, "Shilajit attenuates streptozotocin induced diabetes mellitus and decrease in pancreatic islet superoxide dismutase activity in rats," Phytother. Res. (1995) 9:41-4. Abstract Only.
Biswas, et al., Int J Diab Dev Ctries, Jul.-Sep. 2010, vol. 30, Issue 3, pp. 153-161.
Chowienczyk, et al., "Photoplethysmographic assessment of pulse wave reflection: blunted response to endothelium dependant beta 2-adrenergic vasodilation in type 2 diabetes mellitus," J. Am. Coll. Cardiol. (Dec. 1999) 34(7):2007-14.
Millasseau et al., "Determination of age related increases in large artery stiffness by digital pulse contour analysis," Clinical Science (2002) 103: 371-377.
Miranda, et al., "A Rapid, Simple Spectrophotometric Method for Simultaneous Detection of Nitrate and Nitrite," Nitric Oxide: Biology and Chemistry (2001) vol. 5, No. 1, pp. 62-71. Abstract Only.
Naidu, et al., "Comparison of two β2 adrenoceptor agonists by different routes of administration to assess human endothelial function," Indian J. Pharmacol. (2007) 39:168-9.

(Continued)

*Primary Examiner* — Doan T Phan
(74) *Attorney, Agent, or Firm* — Amin Talati Upadhye LLP; George M. Carrera, Jr.

(57) ABSTRACT

Chromium-three cation containing compositions in synergistic combination with *Phyllanthus emblica* extract and Shilajit are useful for improvement of endothelial function and cardiovascular health, including treatment of type 2 diabetes and metabolic syndrome.

16 Claims, 19 Drawing Sheets

(56) References Cited

OTHER PUBLICATIONS

Schalkwijk, et al., "Vascular complications in diabetes mellitus: the role of endothelial dysfunction," Clinical Science (2005) 109: 143-159.
Trivedi, et al., "Effect of Shilajit on blood glucose and lipid profile in alloxan-induced diabetic rats," Indian J. Pharmacol. (2004) 36(6):.373-376.
Vidyasagar, et al., "Oxidative stress and antioxidant status in acute organophosphorous insecticide poisoning," Indian J. Pharmacol. (Apr. 2004) 36(2): 76-79.
Agarwal, S.P., et al., Shilajit: A Review. Phytother Res. May 2007; 21(5):401-5.
Beckman, Pathophysiology of Vascular Dysfunction in Diabetes. Cardiology Rounds. 2004; 8(10):1-6.
Bendele, Animal models of osteoarthritis. J. Musculoskelet Neuronal Interact. Jun. 2001;1(4):363-76.
Bhattacharyya, et al., Beneficial Effect of Processed Shilajit on Swimming Exercise Induced Impaired Energy Status of Mice. Pharmacology Online. 2009; 1: 817.
Bhattacharya, et al., Effects of shilajit on biogenic free radicals. Phytother. Res. 1995; 9(1): 56-59. Abstract Only.
Bhattacharyya, et al., Shilajit Dibenzo-alpha-Pyrones: Mitochondria Targeted Antioxidants. Pharmacologyonline, 2009; 2: 690-698.
Brandt, Animal models of osteoarthritis. Biorheology. 2002; 39(1-2): 221-35. Abstract Only.
Chipman, SD, et al., Defective proa2(I) collagen synthesis in a recessive mutation in mice: A model of human osteogenesis imperfecta. Proc. Natl. Acad. Sci. Usa, vol. 90, Mar. 1993, pp. 1701-1705.
Curtis, et al., Biological basis for the benefit of nutraceutical supplementation in arthritis. Drug Discov. Today. Apr. 1, 2004; 9(7): 336. Abstract Only.
Fleck, Therapeutic and Safety Evaluation of Crominex 3+ in Moderately Arthritic Dogs, Thesis. Murry State University, May 2013.
Ghosal, Chemistry of shilajit, an immunomodulatory Ayurvedic rasayan. Pure & Applied Chemistry. 1990; vol. 62, Issue 7, pp. 1285-1288.
Ghosal, et al., Interaction of Shilajit with Biogenic Free Radicals. Indian Journal of Chemistry, 1995; p. 596, vol. 34B. Bibliography Only.
Ghosal, et al., Shilajit I: chemical constituents. J. Pharm. Scis. J Pharm Sci. May 1976; 65(5): 772-3.
Ghosal, et al., The Core Structure of Shilajit Humus. Soil Biology & Biochemistry. 1991, p. 673, vol. 23. Abstract Only.
Heinemeier, KM et al. Expression of collagen and related growth factors in rat tendon and skeletal muscle in response to specific contraction types. J Physiol, vol. 582, part 3, Aug. 1, 2007, pp. 1303-1316.
Inzucchi S.E., "Oral Antihyperglycemic Therapy for Type 2 Diabetes," JAMA (2002) 287(3):360-372.
Little et al, Animal Models of Osteoarthritis, Current Rheumatology Reviews, 2008, 4.
Meena, et al., Shilajit: A panacea for high-altitude problems. Int J Ayurveda Res. Jan. 2010; 1(1): 37-40.
Ortolani's sign, in Saunders Comprehensive Veterinary Dictionary, 3rd edition, 2007.
Pandolfi, A., et al., "Chronic hyperglicemia and nitric oxide bioavailability play a pivotal role in pro-atherogenic vascular modifications," Genes Nutr. (2007) 2:195-208.
Potenza, et al., Endothelial Dysfunction in Diabetes: From Mechanisms to Therapeutic Targets. Current Medicinal Chemistry, 2009; 16: 94-112.
Primavie. 2014; 4 pgs.
Slocum, et al., Cranial tibial thrust: a primary force in the canine stifle. J Am Vet Med Assoc.,1983; 183(4): 456-9. Abstract Only.
Thorat, et al., Emblica Officinalis: A Novel Therapy for Acute Pancreatitis—An Experimental Study. HPB Surg. 1995; 9(1): 25-30.
Tiwari, et al., An interpretation on Ayurvedic findings on shilajit. JRIM. 8: 53. Bibliography Only.
Van Den Berg, Lessons from animal models of osteoarthritis. Current Opinion in Rheumatology. 2001; 13(5): 452-456. Abstract Only.
Velmurugan, et al., Evaluation of safety profile of black shilajit after 91 days repeated administration in rats. Asian Pac J Trop Biomed. Mar. 2012; 2(3): 210-4.
Winston, et al., Adaptogens: Herbs for Strength, Stamina, and Stress Relief. 2007; 271.
De Jager et al., "Long-term effects of metformin on endothelial function in type 2 diabetes: a randomized controlled trial," J. Intern. Med. Jan. 2014; 275(1): 59-70.
Tousoulis et al., "Impact of 6 weeks of treatment with low-dose metformin and atorvastatin on glucose-induced changes of endothelial function in adults with newly diagnosed type 2 diabetes mellitus: a single-blind study," Clin. Ther. Sep. 2010; 32(10):1720-8.
Naoyuki Kitao et al., "The effects of vildagliptin compared with metformin on vascular endothelial function and metabolic parameters: a randomized, controlled trial (Sapporo Athero-Incretin Study 3)," Cardiovasc. Diabetol. (2017) 16: 125.
Nesti et al., "Metformin effects on the heart and the cardiovascular system: A review of experimental and clinical data," Nutr. Metab. Cardiovasc. Dis. Aug. 2017; 27(8): 657-669.
Nomoto, H., et al, "A randomized controlled trial comparing the effects of sitagliptin and glimepiride on endothelial unction and metabolic parameters: Sapporo Atheno-Incretin Study 1 (SAIS1)," PLoS One Oct. 6, 2016; 11(10); 1-15.

\* cited by examiner $=p<0.001 compared between the three treatments

CHROMIUM-CONTAINING COMPOSITIONS IN COMBINATION WITH *PHYLLANTHUS EMBLICA* AND SHILAJIT HAVING SYNERGISTIC EFFECTS FOR IMPROVING ENDOTHELIAL FUNCTION AND CARDIOVASCULAR HEALTH

This application is a continuation-in-part of co-pending U.S. patent application Ser. No. 14/718,613, filed on May 21, 2015, which claims the benefit of earlier filed U.S. Provisional Application No. 62/001,438, filed on May 21, 2014, each of which are hereby incorporated by reference herein.

FIELD OF THE INVENTION

The present invention relates to a method for improvement of endothelial function and cardiovascular health by using synergistic compositions containing a chromium complex (Crominex®3+), prepared by complexing chromium with a standardized extract of *Phyllanthus emblica* and Shilajit, and combinations thereof.

BACKGROUND

Cardiovascular disease (CVD) is the number one cause of death globally. More people die annually from CVD than from any other cause. Smoking, hypertension, high LDL cholesterol, low HDL cholesterol and diabetes mellitus (DM) are the five major risk factors for CVD. Diabetes is associated with an increased risk of atherosclerosis, which may result in coronary artery disease (CAD) (A. Pandolfi, et al., "Chronic hyperglycemia and nitric oxide bioavailability play a pivotal role in proatherogenic vascular modifications," *Genes & Nutrition* (2007) 2 (2): 195-208). Physiological impairments that link DM with a marked increase in atherosclerotic vascular disease include platelet hyperreactivity, a tendency for negative arterial remodeling, impaired fibrinolysis, increased inflammation, and endothelial dysfunction.

Endothelial dysfunction, present at disease onset, may be the cause of atherogenesis that is present throughout the course of DM and associated with late-stage adverse outcomes (Panwar, et al., "Atherothrombotic risk factors & premature coronary heart disease in India: A case-control study," *Indian J. Med. Res.* (July 2011) 134: 26-32). The endothelial dysfunction results from reduced bioavailability of the vasodilator nitric oxide (NO) mainly due to accelerated NO degradation by reactive oxygen species (J. A. Beckman, "Pathophysiology of Vascular Dysfunction in Diabetes," *Cardiology Rounds* (December 2004) Volume 8, Issue 10). A currently favored hypothesis is that oxidative stress, through a single unifying mechanism of superoxide production, is the common pathogenic factor leading to insulin resistance, β-cell dysfunction, impaired glucose tolerance (IGT) and ultimately to Type 2 DM (T2DM). Furthermore, this mechanism has been implicated as the underlying cause of both the macrovascular and microvascular complications associated with Type 2 DM. It follows that therapies aimed at reducing oxidative stress would benefit both patients with T2DM and those at risk for developing diabetes (Potneza, et al., "Endothelial Dysfunction in Diabetes: From Mechanism to Therapeutic Targets," *Current Medicinal Chemistry* (2009) 16: 94-112; S. E. Inzucchi, "Oral Antihyperglyccmic Therapy for Type 2 Diabetes. Scientific Review and Clinical Applications," *Journal of American Medical Association* (Jan. 16, 2002—Vol 287, No. 3, pp. 360-372; and Wright, et al., "Oxidative stress in type 2 diabetes: the role of fasting and postprandial glycaemia," *Int. J. Clin. Pract.* (2006 March) 60(3): 308-314).

Many natural product compositions possess potent antioxidant, anti-inflammatory and cardio-protective properties and are used by patients with increased risk of cardiovascular morbidity and mortality in order to treat or prevent disease and/or reduce symptoms. Among them, *Phyllanthus emblica*, syn. *Emblica officinalis* Gaertn., the Indian gooseberry (PE, "Amla") is widely used in Indian medicine for the treatment of various diseases. There are studies which show significant anti-hyperglycaemic and lipid lowering effects of PE in diabetic patients. In in-vitro and animal studies, PE demonstrates potent antioxidant effects against several test systems such as superoxide radical and hydroxyl radical scavenging action, and in systemic augmentation of antioxidant enzymes in animals (Antony, et al., "A pilot clinical study evaluate the effect of *Emblica officinalis* extract (Amlamax™) on markers of systemic inflammation and dyslipidemia," *Indian J. Clin. Biochemistry* (2008) 23(4): 378-381).

In addition, Shilajit is an herbo-mineral drug, which oozes out from a special type of Himalayan mountain rocks in the peak summer months. It is found at high altitudes ranging from 1000-5000 meters. The active constituents of Shilajit contain dibenzo-alpha-pyrones, fulvic acids and related metabolites, small peptides (constituting non-protein amino acids), some lipids, and carrier molecules (fulvic acids). See, Ghosal, S., et al., "Shilajit Part 1—Chemical constituents," *J. Pharm. Sci.* (1976) 65:772-3; Ghosal, S., et al., "Shilajit Part 7—Chemistry of Shilajit, an immunomodulatory ayurvedic rasayana," *Pure Appl. Chem.* (IUPAC) (1990) 62:1285-8; Ghosal, S., et al., "The core structure of Shilajit humus," *Soil Biol. Biochem.* (1992) 23:673-80; and U.S. Pat. Nos. 6,440,436 and 6,869,612 (and references cited therein); all hereby incorporated by reference herein.

Shilajit (PrimaVie®) finds extensive use in Ayurveda, for diverse clinical conditions. For centuries people living in the isolated villages in Himalaya and adjoining regions have used Shilajit alone, or in combination with, other plant remedies to prevent and combat problems with diabetes (Tiwari, V. P., et al., "An interpretation of Ayurvedica findings on Shilajit," *J. Res. Indigenous Med.* (1973) 8:57). Moreover being an antioxidant it will prevent damage to the pancreatic islet cell induced by the cytotoxic oxygen radicals (Bhattacharya S. K., "Shilajit attenuates streptozotocin induced diabetes mellitus and decrease in pancreatic islet superoxide dismutase activity in rats," *Phytother. Res.* (1995) 9:41-4; Bhattacharya S. K., "Effects of Shilajit on biogenic free radicals," *Phytother. Res.* (1995) 9:56-9; and Ghosal, S., et al., "Interaction of Shilajit with biogenic free radicals," *Indian J. Chem.* (1995) 34B:596-602). It has been proposed that the derangement of glucose, fat and protein metabolism during diabetes, results in development of hyperlipidemia. In one study, Shilajit produced significant beneficial effects on lipid profile in rats (Trivedi N. A., et al., "Effect of Shilajit on blood glucose and lipid profile in alloxan-induced diabetic rats," Indian J. Pharmacol. (2004) 36(6):373-376). Further, Chromium 3+(Cr 3+) helps insulin metabolize fat, turn protein into muscle, and convert sugar into energy. Chromium-activated insulin considerably increases the amount of blood sugar available for energy production. Some of the other chromium compounds available as supplements are Chromium chloride, Chromium picolinate, Chromium polynicotinate, and Chromium dinicocysteinate.

Crominex®3+, which is a complex of chromium with the polyphenolic compounds of *Phyllanthus emblica* and Shilajit, as described herein in embodiments of the present invention surprisingly exhibited improvement in endothelial function and blood lipid profile in type 2 diabetics as well as individuals with symptoms of metabolic syndrome, although it contains very small amounts of *Phyllanthus emblica* and Shilajit (3 mg of each per 200 mcg dose of chromium, and 6 mg each per 400 mcg dose of chromium, respectively). Both *Phyllanthus emblica* and Shilajit are usually effective in doses of 250 or 500 mg per dose. For example, U.S. Pat. No. 8,962,576 describes a composition and method of improving endothelial function and cardiovascular health using *Phyllanthus emblica* extract at 250 mg and 500 mg twice a day dosing (which is equivalent to 500 mg and 1000 mg per day). Similarly, U.S. Patent Application Publication US2014/0079729A1 describes a method of improving endothelial function and decreasing cardiovascular morbidity using Shilajit at 250 mg twice a day dosing (which is equivalent to 500 mg per day). However, a combination of Chromium, *Phyllanthus emblica* extract and Shilajit surprisingly exhibited effectiveness in improving endothelial function and cardiovascular risk parameters, although the concentrations of *Phyllanthus emblica* extract and Shilajit are very low as discussed above and described herein.

Thus, it would be advantageous to have a composition with small amounts of chromium and small amounts of *Phyllanthus emblica* and Shilajit which would significantly improve endothelial function and cardiovascular risk factors.

SUMMARY

An objective of the present invention is to develop a method of using trivalent chromium in combination with *Phyllanthus emblica* extract and Shilajit for improving endothelial function and cardiovascular health in patients with Type 2 diabetes mellitus as well as in healthy subjects with metabolic syndrome symptoms. It has been shown that methods using the combination of trivalent chromium cation, *Phyllanthus emblica* extract and Shilajit exhibit synergism with regard to improvements in endothelial function and cardiovascular risk factors, particularly in individuals suffering from type 2 diabetes mellitus or metabolic syndrome symptoms.

A method of treating or preventing endothelial dysfunction is provided including administering to an individual in need thereof an effective amount of a composition comprising trivalent chromium in combination with *Phyllanthus emblica* extract and Shilajit, wherein endothelial function and cardiovascular risk factors are improved or mitigated in a synergistic manner.

Other embodiments are contemplated for the effective treatment of human patients having type 2 diabetes mellitus (T2DM). In one embodiment, a method of treating a diabetic individual suffering from type 2 diabetes mellitus includes administering to an individual in need thereof an effective amount of a composition comprising trivalent chromium in combination with *Phyllanthus emblica* extract and Shilajit, wherein endothelial function, as measured by the levels of one or more markers of oxidative stress and/or inflammation, and cardiovascular risk factors, such as total cholesterol, HDL, LDL, triglycerdies, hsCRP and HbA1c, are improved significantly and in a synergistic manner.

In another embodiment, a method of treating a diabetic individual suffering from type 2 diabetes mellitus includes administering to an individual in need thereof an effective amount of a composition comprising trivalent chromium in combination with *Phyllanthus emblica* extract and Shilajit, wherein a blood lipid parameter is improved, or one or more cardiovascular risk parameters are improved or mitigated in a synergistic manner.

In another embodiment, a method of treating an individual with metabolic syndrome symptoms includes administering to an individual in need thereof an effective amount of a composition comprising trivalent chromium in combination with *Phyllanthus emblica* extract and Shilajit, wherein endothelial function is improved in a synergistic manner as measured by the levels of one or more markers of oxidative stress and/or inflammation.

In yet another embodiment, a method of treating an individual with metabolic syndrome symptoms includes administering to an individual in need thereof an effective amount of a composition comprising trivalent chromium in combination with *Phyllanthus emblica* extract and Shilajit, wherein a blood lipid parameter is improved, or one or more cardiovascular risk parameters is improved in a synergistic manner.

DETAILED DESCRIPTION

Figure 1:
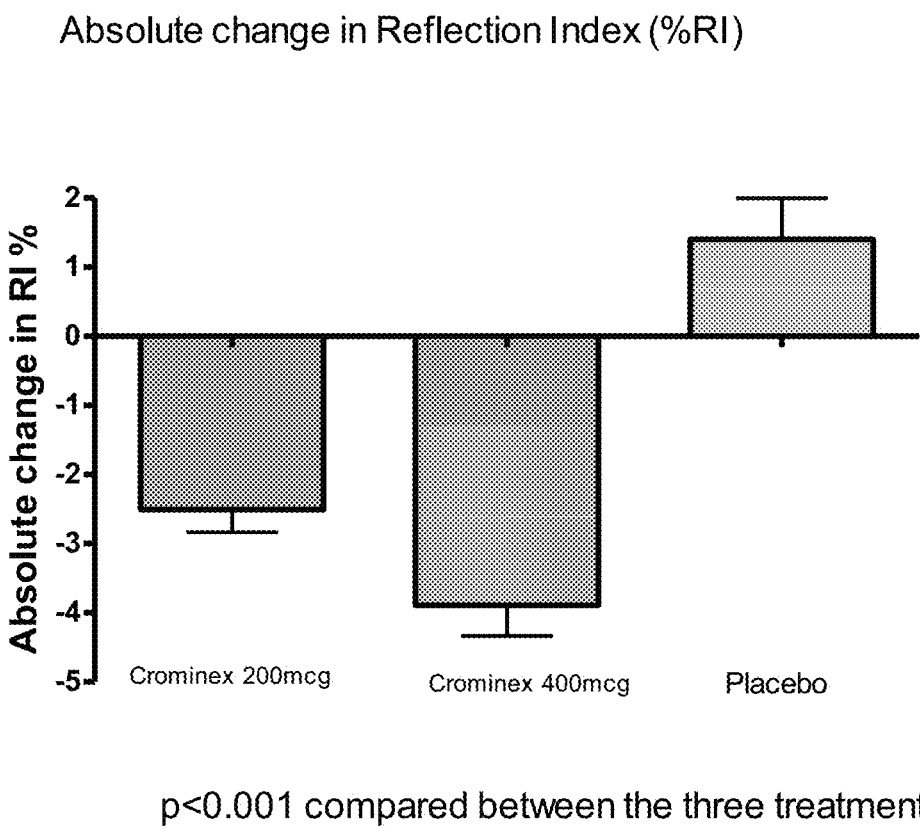
FIG. 1 illustrates absolute change in reflective index (RI %) in type 2 diabetic patients before and after 12 weeks treatment in one embodiment in accordance with the present invention with Crominex®3+ 200 mcg and Crominex®3+ 400 mcg, as described in Table 3.
Figure 2:
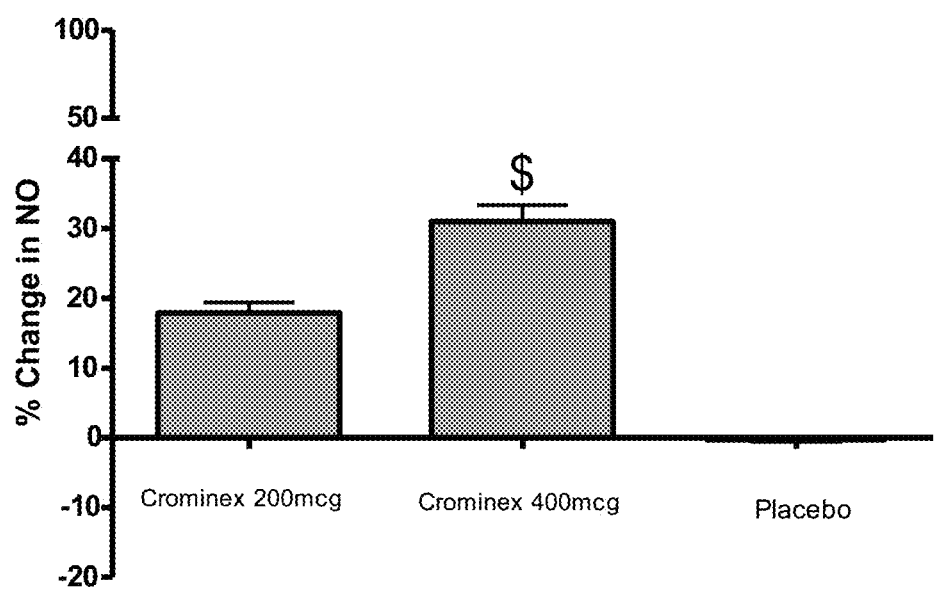
FIG. 2 illustrates mean percent change in nitric oxide (NO) concentration level in type 2 diabetic individuals before and after 12 weeks treatment in one embodiment in accordance with the present invention with Crominex®3+ 200 mcg and Crominex®3+ 400 mcg, as described in Table 5.
Figure 3:
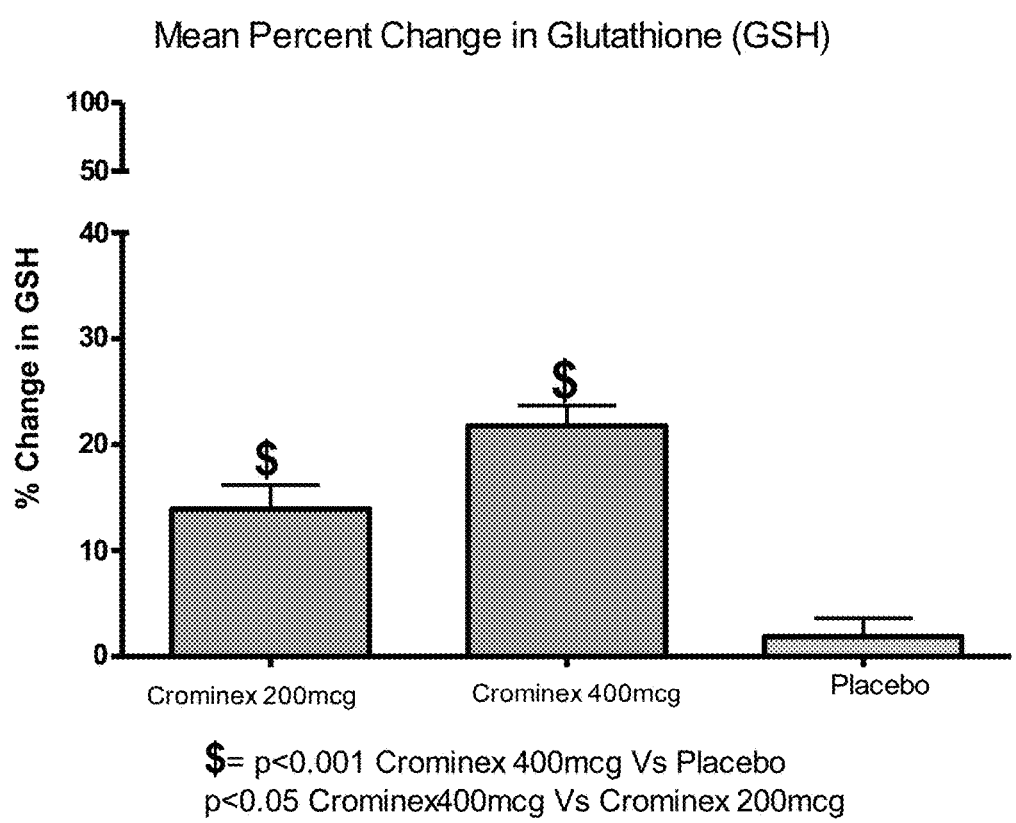
FIG. 3 illustrates mean percent change in glutathione (GSH) concentration level in type 2 diabetic individuals before and after 12 weeks treatment in one embodiment in accordance with the present invention with Crominex®3+ 200 mcg and Crominex®3+ 400 mcg, as described in Table 5.
Figure 4:
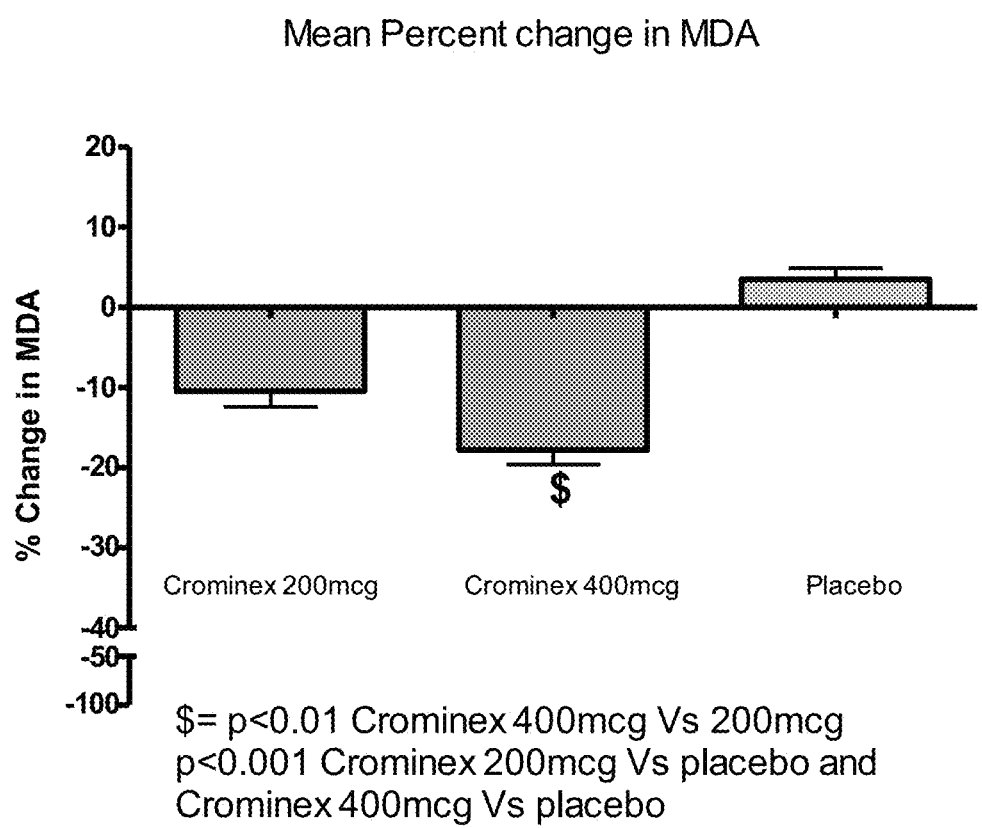
FIG. 4 illustrates mean percent change in malondialdehyde (MDA) concentration level in type 2 diabetic individuals before and after 12 weeks treatment in one embodiment in accordance with the present invention with Crominex®3+ 200 mcg and Crominex®3+ 400 mcg, as described in Table 5.
Figure 5:
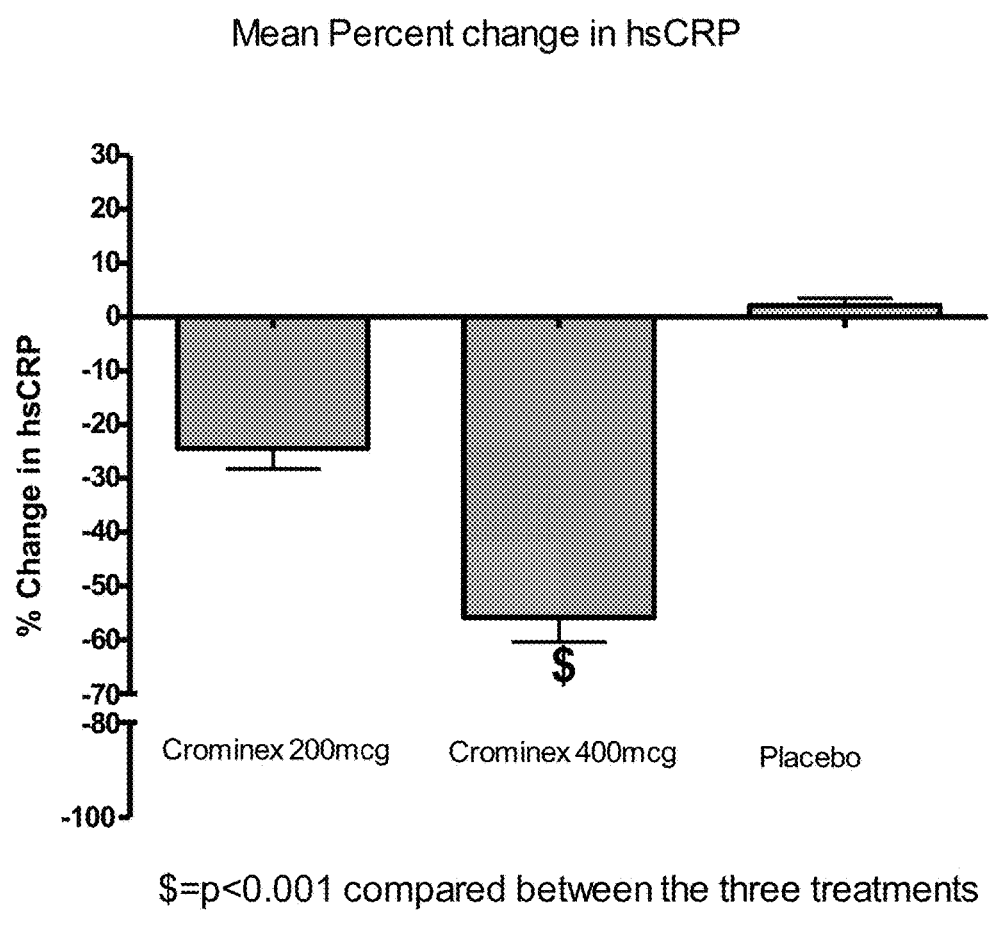
FIG. 5 illustrates mean percent change in high sensitivity C-reactive protein (hs-CRP) concentration level in type 2 diabetic individuals before and after 12 weeks treatment in one embodiment in accordance with the present invention with Crominex®3+ 200 mcg and Crominex®3+ 400 mcg, as described in Table 5.
Figure 6:
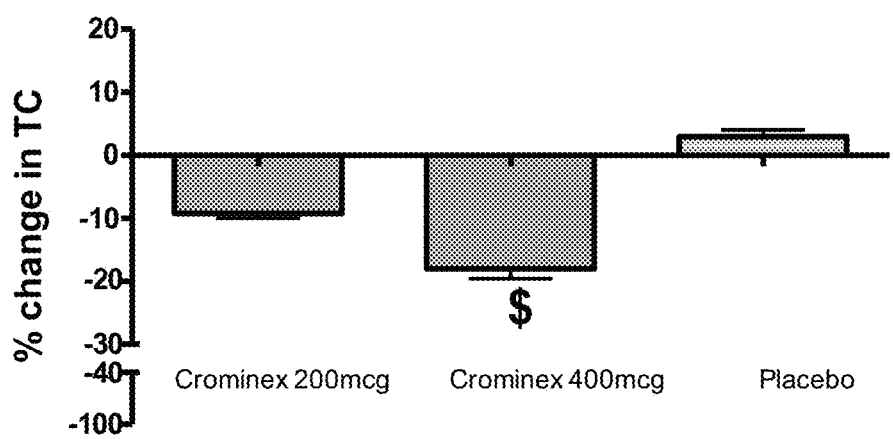
FIG. 6 illustrates mean percent change in total cholesterol (TC) concentration level in type 2 diabetic individuals before and after 12 weeks treatment in one embodiment in accordance with the present invention with the present invention with Crominex®3+ 200 mcg and Crominex®3+ 400 mcg, as described in Table 6B.
Figure 7:
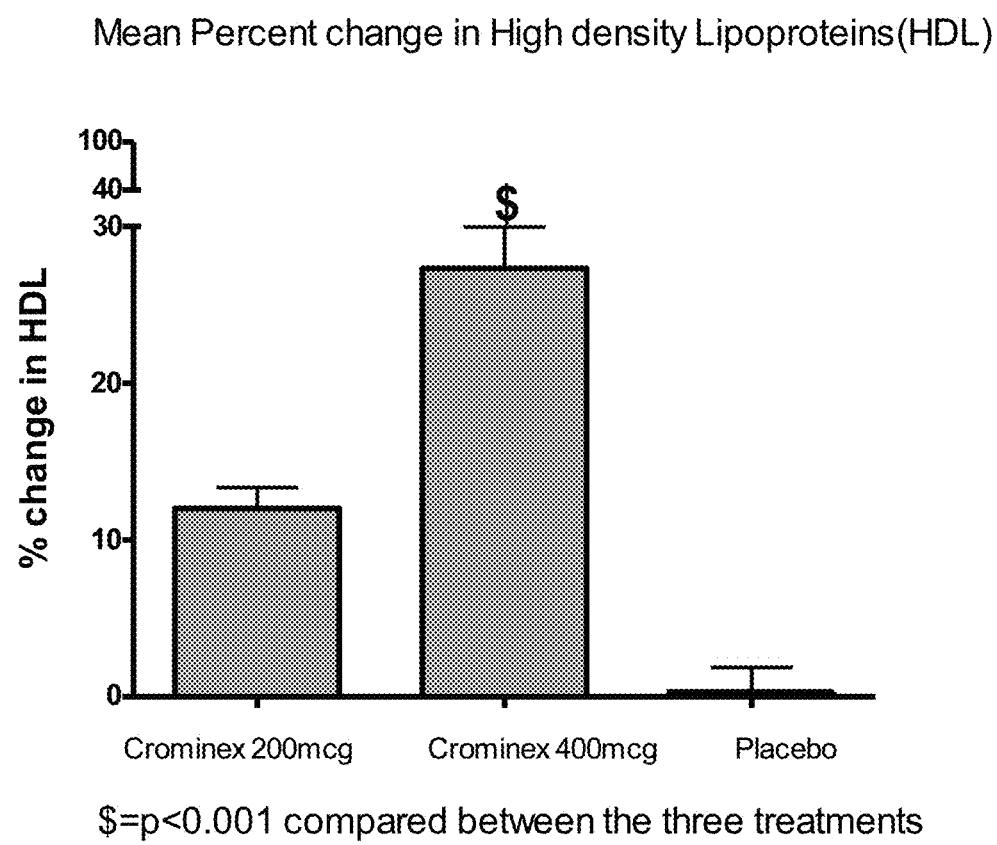
FIG. 7 illustrates mean percent change in HDL-C concentration level in type 2 diabetic individuals before and after 12 weeks treatment in one embodiment in accordance with the present invention with the present invention with Crominex®3+ 200 mcg and Crominex®3+ 400 mcg, as described in Table 6B.
Figure 8:
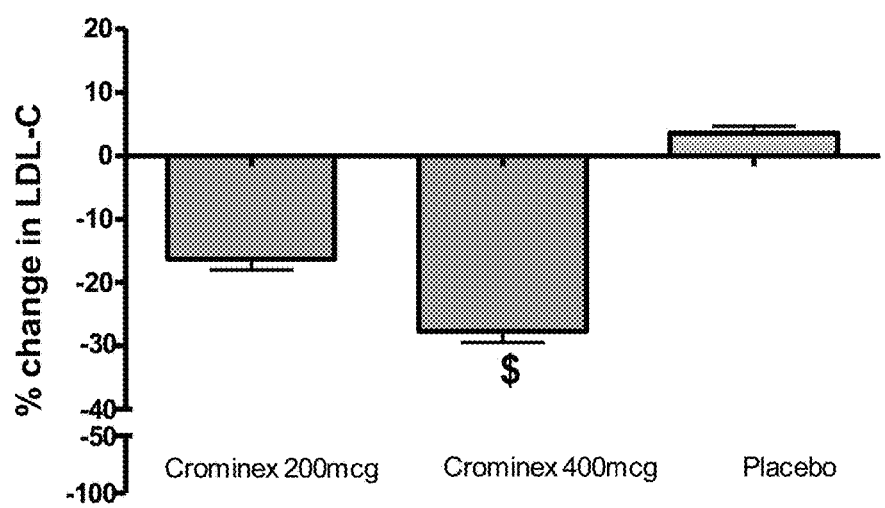
FIG. 8 illustrates mean percent change in LDL-C concentration level in type 2 diabetic individuals before and after 12 weeks treatment in one embodiment in accordance with the present invention with the present invention with Crominex®3+ 200 mcg and Crominex®3+ 400 mcg, as described in Table 6B.
Figure 9:
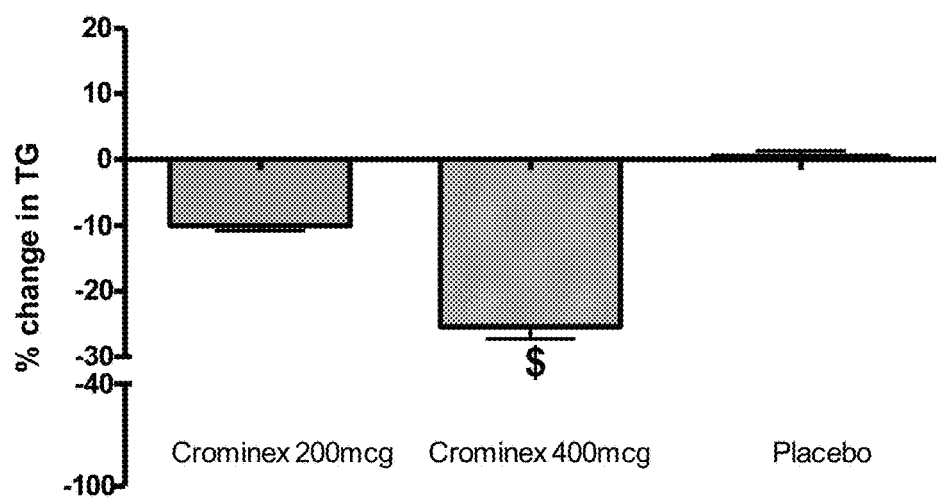
FIG. 9 illustrates mean percent change in triglycerides (TG) concentration level in type 2 diabetic individuals before and after 12 weeks treatment in one embodiment in accordance with the present invention with the present invention with Crominex®3+ 200 mcg and Crominex®3+ 400 mcg, as described in Table 6B.
Figure 10:
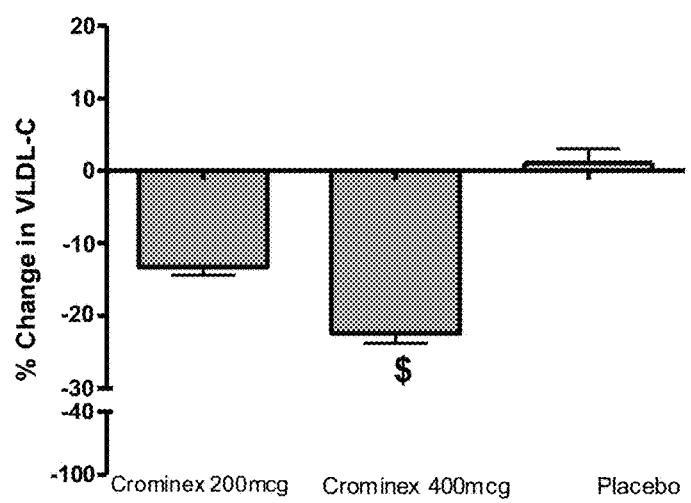
FIG. 10 illustrates mean percent change in VLDL-C concentration level in type 2 diabetic individuals before and after 12 weeks treatment in one embodiment in accordance with the present invention with the present invention with Crominex®3+ 200 mcg and Crominex®3+ 400 mcg, as described in Table 6B.

A chromium complex (Crominex®3+), prepared by complexing trivalent chromium with small amounts of standardized extract of *Phyllanthus emblica* and Shilajit, has been clinically studied in type 2 diabetic patients as well as subjects with metabolic syndrome symptoms in two separate studies, and it was surprisingly discovered that Crominex®3+, despite the fact that it contains very small doses of *Phyllanthus emblica* extract and Shilajit, has significantly reduced total cholesterol, LDL cholesterol, triglycerides, highly sensitive C-reactive protein (hsCRP), and HbA1c levels, and improved endothelial function and HDL Cholesterol levels in the blood. Based on this observation, two more clinical studies were conducted on the individual components of Crominex®, i.e., trivalent chromium chloride, *Phyllanthus emblica* extract plus Shilajit, and three other branded chromium supplements available in the market.

These additional studies have confirmed that Crominex® has a significant synergistic activity and is the most efficacious of all the products studied.

In another aspect, the present invention reveals the usefulness of trivalent chromium in combination with *Phyllanthus emblica* extract and Shilajit for improvement of endothelial function and cardiovascular health in a human patient or in an animal.

Animal subjects include large domestic mammals, for example, cows or cattle (or other bovine species), horses, pigs, sheep, goats, other livestock, and the like. Animal subjects may also include smaller domestic mammals, such as, but not limited to, dogs, cats, rabbits, and rodents including rats, mice, hamsters, gerbils, guinea pigs, and the like.

One suitable composition used herein is an extract blend which is isolated in stable form from the fruit of the *Phyllanthus emblica* plant, as described in detail in U.S. Pat. No. 6,124,268. The extraction process includes treating the finely-pulped fruit with a dilute aqueous or alcoholic-water salt solution, e.g. a 0.1 to 5% (w/w) sodium chloride solution, or the like, preferably at about 70° C. 5° C., or with a buffer solution, e.g. 0.1 to 5% (w/w) of sodium citrate/citric acid, or the like, filtering and drying, to provide the extract in powder form.

The extract includes the active constituents Emblicanin-A and Emblicanin-B, which are gallic/ellagic acid derivatives of 2-ketoglucono-6-lactone, in an amount by weight of about 35-55%, as well as: Punicagluconic acid, also named punigluconin (about 4-15% by weight), Pedunculagin (about 10-20% by weight), Rutin (about 5-15% by weight), and low-to-medium molecular weight tannoids of gallic/ellagic acid (about 10-30% by weight), gallic acid (up to about 5% by weight), and ellagic acid (up to about 5% by weight). Note that taken together, the overall extracted mixture or blend comprises an isolatable, identifiable, and purifiable group of components comprising a group of low molecular weight hydrolyzable tannoids ("LMwHTs"), generally excluding free gallic acid and ellagic acid. The composition may further include a nutraceutically or pharmaceutically acceptable carrier.

In one suitable embodiment, the amount of LMwHTs contained in a purified and/or enriched extract of *Phyllanthus emblica* is at least about 60% by weight. In another embodiment, the amount of LMwHTs contained in a purified and/or enriched extract of *Phyllanthus emblica* is greater than about 60% by weight. In another embodiment, the amount of LMwHTs contained in a purified and/or enriched extract of *Phyllanthus emblica* is greater than about 70% by weight. CAPROS® (available from Natreon, Inc., New Brunswick, N.J.) is one such exemplary extract of *Phyllanthus emblica*.

Shilajit (PrimaVie®, available from Natreon, Inc., New Brunswick, N.J.) is a standardized dietary supplement ingredient extracted and processed from Shilajit bearing rocks, containing not less than about 50% to 60% by weight fulvic acids (FAs), at least about 10% by weight dibenzo-α-pyrone chromoproteins, and at least 0.3%, or more, by weight total dibenzo-α-pyrones (DBPs). Water content is about 6%, or less, by weight. Water-soluble extractive value is about 80% (w/w), or greater.

In an embodiment, a suitable daily dose of each of an extract of *Phyllanthus emblica* and Shilajit is in a range of from about 3 mg to about 100 mg, and the daily dose of trivalent chromium in a range from about 100 mcg to about 1000 mcg. In another embodiment, the daily dose of each of an extract of *Phyllanthus emblica* and Shilajit is in a range of from about 3 mg to about 100 mg, and the daily dose of trivalent chromium in a range from about 200 mcg to about 500 mcg.

Patients with diabetes have vascular complications and endothelial dysfunction is one of the early prognostic markers of atherosclerosis which may eventually result in cardiovascular disease. Studies have reported that endothelial dysfunction occurs in patients with diabetes much earlier than clinical manifestations of diabetic vascular complications (Schalkwijk, et al., "Vascular complications in diabetes mellitus: the role of endothelial dysfunction," *Clinical Science* (2005) 109: 143-159). Diabetes is associated with accelerated atherosclerosis and microvascular complications are a major cause of morbidity and mortality, as discussed above. Endothelial cell dysfunction is emerging as a key component in the pathophysiology of cardiovascular abnormalities associated with diabetes mellitus.

Increased arterial stiffness, as measured by pulse wave analysis, is associated with cardiovascular risk factors and established coronary artery disease. Pulse wave analysis is simple and reproducible to stratify cardiac risk in diabetes. Whilst arterial compliance is determined predominantly by structural factors, the vascular endothelium is also involved. The vascular endothelium contributes to vascular tone and endothelial dysfunction is implicated as an early functional alteration predating structural changes of the vasculature. Conventional cardiac risk factors such as dyslipidemia, hypertension, smoking, and Type 2 diabetes are associated with impaired endothelial function. The intact endothelium promotes vasodilatation principally via the release of NO—originally also called endothelium derived relaxing factor. Endothelium dependent vasodilators reduce pulse wave velocity suggesting nitric oxide (NO) plays a role in determining arterial distendability. Free radical NO has emerged as a fundamental signaling device regulating virtually every critical cellular function and is a potent mediator of cellular damage in many conditions. Nitric oxide is produced in endothelial cells from the substrate L-Arginine via endothelial Nitric oxide synthatase (eNOS). Elevated asymmetric dimethylarginine levels cause coupling, a mechanism which leads to decreased NO bioavailability. The endothelial dysfunction associated with diabetes has been attributed to lack of bioavailable nitric oxide due to reduced ability to synthesize NO from L-Arginine. New basic research insights provide possible mechanisms underlying the impaired NO bioavailability in Type 2 diabetes.

Use of herbs for the treatment of cardiovascular diseases and diabetes in Ayurveda, Chinese and Unani systems of medicine has provided a new lead to understanding the pathophysiology of these diseases. Therefore, it is rational to use our natural resources for identifying and selecting inexpensive and safer approaches for the management of cardiovascular disease along with current therapy. For example, Shilajit provides potential benefits for the diabetic patient (Bhattacharya S. K., "Shilajit attenuates streptozotocin induced diabetes mellitus and decrease in pancreatic islet superoxide dismutase activity in rats," *Phytother. Res.* (1995) 9:41-4), and may also provide significant beneficial effects in lipid profile (Trivedi N. A., et al., "Effect of Shilajit on blood glucose and lipid profile in alloxan-induced diabetic rats," *Indian J. Pharmacol.* (2004) 36(6):373-376).

Oxidative stress induced by reactive oxygen species (ROS) also plays an important role in the etiology of atherosclerosis and coronary heart disease. Recent research has suggested that oxidative stress is one of the mechanisms involved in endothelial dysfunction. Wide spread attention has been focused on involvement of oxygen free radicals in pathogenesis of diabetes. Cellular enzymatic (e.g., superoxide dismutase or "SOD") and non enzymatic antioxidants (glutathione or "GSH") act as primary line of defense to cope with the deleterious effect of these radical species. Earlier studies showed the beneficial effects of Amla on atherosclerosis and dyslipidemia (Antony, et al.).

Hypercholesterolemia is a major risk factor for the development of atherosclerosis and is associated with coronary and peripheral vascular disease. Several lines of evidence show that the improvement and incidence of coronary artery disease (CAD) is associated with lowering hypercholesterolemia. To treat hypercholesterolemia, extensive interventions are recommended including diet control, exercise and the use of hypocholesterolemic drugs. However some patients cannot tolerate the adverse events from these drugs, such as liver damage which necessitates the use of other safer and efficacious alternative medications. One research group evaluated the anti-hyperglycemic and lipid lowering properties of *Phyllanthus emblica* in normal and diabetic human volunteers (Akhtar, et al., "Effect of Amla fruit (*Emblica officinalis* Gaertn.) on blood glucose and lipid profile of normal subjects and type 2 diabetic patients," *Int. J. Food Sci. Nutr.* (2011) 62(6): 609-616). In this study, significant decreases were observed in total cholesterol (TC) and triglycerides (TG), and increases were observed in high density lipoprotein-cholesterol (HDL-C) in normal and diabetic volunteers receiving 2 or 3 g of *Phyllanthus emblica* powder per day. In another study of *Phyllanthus emblica* significant reduction in TC, LDL (low density lipoprotein) and TG was reported, whereas there was significant elevation of HDL (high density lipoprotein) (Antony, et al.). The results of their study at doses of 500 mg/day and 1000 mg/day brought significant reduction in the level of risk factors arising from dyslipidemia and inflammation. The exact mechanism by which the fruit of *P. emblica* exerts a beneficial effect is presently not clear. Without intending to be bound by theory, it is believed that *P. emblica*, like statins, possesses HMG CoA reductase inhibitory activity. Thus, *P. emblica* is believed to exert beneficial effects on cardiovascular parameters (Anita, et al., "Flavonoids from *Emblica Officinalis* and *Mangifera indica*-effectiveness for dyslipidemia," *J. Ethnopharmacol.* (2002) 79:81-7).

A precursor formulation for Crominex® 3+ was evaluated and published with title "Effects of adjunct therapy of a proprietary herbochromium supplement (HCrS) in type 2 diabetes: randomized clinical trial" (Biswas, et al., Int J Diab Dev Ctries, July-September 2010, Volume 30, Issue 3, pp. 153-161). In this study, the precursor formulation was studied as adjunct therapy at 400 mcg per day chromium dose in type 2 diabetics who are being treated with oral anti-diabetic drugs metformin, glipizide and pioglitazone. The results indicate that none of the cardiovascular parameters tested showed any statistically significant improvement compared to the placebo group. This formulation had the same ingredients in the same proportions as the Crominex® 3+ formulation, but was processed differently. After the ingredients were mixed in water, the dispersion was dried under vacuum at 45° C. in a Rotovap®, possibly destroying the bioactive polyphenolic compounds in *Phyllanthus emblica*. In distinct comparison, Crominex® 3+ product is manufactured by mixing the ingredients in water and spray drying the dispersion, which exposes the bioactives to heat for only a few seconds, thus preserving their activity. This preservation of the bioactives by spray drying may explain the significant clinical efficacy of Crominex® 3+ compared to the precursor formulation of Biswas, et al. In an alternative embodiment, the Crominex® 3+ product is manufactured using freeze drying or lyophilization. In general, the manufacturing processes employed minimize exposure to heat to prevent loss of efficacy in the finished products.

A published patent application, U.S. 20050085454, titled "Phenolic antioxidant chromium complexes for treatment or prevention of type 2 diabetes or glucose intolerance" describes a phenolic antioxidant-chromium complex for treating, preventing or maintaining a condition in primates, especially humans, particularly Type 2 diabetes or glucose intolerance, and more particularly, it relates to chromium complexed with agents which are low molecular weight hydrolyzable tannins of plant origin and/or purified Shilajit containing oxygenated dibenzo-.alpha.-pyrone (DBP) or its conjugates, including dimers and oligomers and fulvic acids, obtained by extraction of native Shilajit, and pharmaceutical and nutritional compositions thereof, useful for supplementing dietary chromium, lowering blood glucose and serum lipid, including the lowering of undesirably high blood serum LDL-cholesterol levels and the raising of blood serum HDL-cholesterol levels and increasing lean body mass. However, the disclosures of this application are not based on any clinical data.

The clinical efficacy of Crominex® 3+ described above may be further understood by the following Examples 1 and 2 of clinical studies with Crominex® 3+, which were conducted in the Department of Clinical Pharmacology and Therapeutics, Nizam's Institute of Medical Sciences, Hyderabad, India.

In the present studies the product used is Crominex® (Natreon, Inc., New Brunswick, N.J.) which contains Chromium chloride ($CrCl_3.6H_2O$), *Phyllanthus emblica* fruit extract, processed Shilajit and microcrystalline cellulose in a proportion of 1:3:3:3 (wt. ratio).

CLINICAL STUDIES DEMONSTRATING EFFICACY OF CROMINEX®

Example 1: Clinical Study on Crominex® 3+ in Type 2 Diabetics

Study Design:
The present clinical study is a prospective, randomized, double blind, placebo-controlled study. Patients of either sex, aged 30-65 years, fasting plasma glucose of 110-126 mg/dl, a glycosylated hemoglobin (HbA1c) between 6.5% and 8% and taking stable dose of anti-diabetic treatment (metformin 1500-2000 mg/day) for the past 8 weeks prior to the screening visit; and having endothelial dysfunction defined as ≤6% change in reflection index (RI) on post salbutamol challenge test were included in the study. Patients with severe uncontrolled hyperglyceamia, uncontrolled hypertension, cardiac arrhythmia, impaired hepatic or renal function, history of malignancy or stroke, smoking, chronic alcoholism, any other serious disease requiring active treatment and treatment with any other herbal supplements, were excluded from the study.

After screening, all the eligible subjects were randomized to receive either one of the three treatments orally for duration of 12 weeks—Group1—one capsule of Crominex®3+, 200 mcg once daily, Group 2—one capsule Crominex®3+, 400 mcg once daily; Group 3—one capsule of placebo once daily.

Subjects were required for follow up at 4, 8 and 12 weeks of therapy. At each visit they were evaluated for efficacy and safety. Pharmacodynamic evaluation for endothelial function was conducted at every visit. Blood samples were collected for evaluation of biomarkers before and at the end of treatment. Safety lab investigations for hematological, hepatic and renal biochemical parameters were conducted before and at the end of the study and also as and when required (in case of any adverse drug reaction (ADR). Subjects were enquired for the presence of ADR and the same was recorded in the case report form. Compliance to therapy was assessed by pill count method.

The active ingredients used in the capsules have the following compositions.

Crominex®3+ may be described broadly as a complex of Chromium with the polyphenols in *Phyllanthus emblica*, such complex (called Chromium emblicate) being incorporated into the fulvic acid structure of Shilajit to improve bioavailability. Cr 3+ is about 200 mcg in 10-12 mg of Crominex®. Crominex®3+ is a chromium supplement available commercially from Natreon, Inc., New Brunswick, N.J., and is a combination of trivalent chromium, *Phyllathus emblica* and Shilajit. For every 200 mcg dose of trivalent chromium, Crominex® 3+ contains 3 mg of *Phyllanthus emblica* extract and 3 mg of Shilajit extract and less than 3 mg of microcrystalline cellulose as a filler.

Capros® (available from Natreon, Inc., New Brunswick, N.J.) is a standardized extract of *Phyllanthus emblica* containing at least 60%, and up to about 70%, low molecular weight hydrolysable tannins, including Emblicanin-A, Emblicanin-B, Punigluconin and Pedunculagin as active ingredients.

Procedure for Assessment of Endothelial Function by Determination of Reflection Index (RI).

A salbutamol (albuterol) challenge test employing digital volume plethysmography was used to assess endothelial function as reported by Chowienczyk et al., "Photoplethysmographic assessment of pulse wave reflection: blunted response to endothelium dependant beta 2-adrenergic vasodilation in type 2 diabetes mellitus," *J. Am. Coll. Cardiol.* (1999 December) 34(7):2007-14; and Naidu, et al., "Comparison of two $\beta_2$ adrenoceptor agonists by different routes of administration to assess human endothelial function," *Indian J. Pharmacol.* (2007) 39:168-9. The patients were examined in supine position after 5 minutes of rest. A digital volume pulse (DVP) was obtained using a photo plethysmograph (Pulse Trace PCA2, PT200, Micro Medical, Gallingham, Kent, UK) transmitting infrared light at 940 nm, placed on the index finger of the right hand. The signal from the plethysmograph was digitized using a 12 bit analogue to digital converter with a sampling frequency of 100 Hz. DVP waveforms were recorded over 20 second period and the height of the late systolic/early diastolic portion of the DVP was expressed as a percentage of the amplitude of the DVP to yield the reflection index (RI), per the procedure described in detail by Millasseau et al., "Determination of age related increases in large artery stiffness by digital pulse contour analysis," *Clinical Science* (2002) 103: 371-377. Three DVP recordings were taken, and measurements of reflection index (RI) were calculated and the mean value was determined. Patients were then administered 400 μg of salbutamol by inhalation. After 15 minutes three measurements of RI were obtained again and the difference in mean RI before and after administration of salbutamol was used for assessing endothelial function. A change of ≤6% in RI post-salbutamol was considered as endothelial dysfunction.

Biomarker Evaluation.

Nitric oxide, MDA, Glutathione and levels were estimated spectrophotometrically as follows. Malondialdehyde (MDA) levels were determined as described in Vidyasagar, et al., "Oxidative stress and antioxidant status in acute organophosphorous insecticide poisoning," *Indian J. Pharmacol.* (April 2004) 36(2): 76-79. Glutathione levels were determined as described in G. L. Ellman, *Arch. Biochem. Biophys.* (1959) 82: 70-77 (original determination). Nitric oxide levels were estimated spectrophotometrically as described in Miranda, et al., "A Rapid, Simple Spectrophotometric Method for Simultaneous Detection of Nitrate and Nitrite," NITRIC OXIDE: *Biology and Chemistry* (2001) Vol. 5, No. 1, pp. 62-71. hsCRP (high sensitivity C-reactive protein) was determined by ELISA method.

Safety Assessments.

All the subjects had undergone complete physical examination, safety lab evaluations at baseline and at the end of the treatment. Samples were collected after an overnight fast of 12 hrs after the last dose of medication for determination of hemoglobin, glycosylated hemoglobin (HbA1c), blood urea, serum creatinine, liver function, lipid profile (Total cholesterol, High density lipoprotein cholesterol (HDL-C), low density lipoprotein cholesterol (LDL-C) using appropriate standard techniques.

Primary and Secondary Efficacy Parameters.

The primary efficacy measure was a change in endothelial dysfunction as assessed by more than 6% change in reflection index at 12 weeks. Secondary efficacy parameters include change in oxidative stress markers, serum levels of nitric oxide at 12 weeks in all the treatment groups. Additionally, safety and tolerability assessment of the test medications were also conducted.

Data Analysis.

Data are expressed as mean±SD. ANOVA and paired and unpaired t-test were performed for within group and between groups analysis respectively. A p-value<0.05 was considered to be statistically significant. All statistical analyses were performed using the Prism Graphpad 4 (GraphPad Software, Inc., La Jolla, Calif., USA).

Results of Study:

60 eligible subjects completed the study. Detailed demographic characteristics of the three study groups are shown in Table 1. There was no significant difference between treatment groups in baseline characteristics including age, weight and body mass index.

TABLE 1

Demographic characteristics of all study groups

| Parameter | Crominex ®3+ 200 mcg | Crominex ®3+ 400 mcg | Placebo |
|---|---|---|---|
| No. of subjects | 20 | 20 | 20 |
| Age in Yrs | 52.25 ± 5.96 | 53.15 ± 6.20 | 56.45 ± 6.96 |
| Gender (M/F) | 12/8 | 14/6 | 11/7 |
| Bodyweight (Kg) | 68.60 ± 4.61 | 66.90 ± 5.42 | 64.06 ± 3.59 |
| BMI (Kg/m$^2$) | 25.14 ± 2.05 | 24.17 ± 1.83 | 24.56 ± 1.38 |

TABLE 2

Effect of Crominex ®3 + 200 mcg, 400 mcg and Placebo on RI (measure of endothelial function)

| Parameter | Crominex ®3 + 200 mcg (n = 20) | | Crominex ®3 + 400 mcg (n = 20) | | Placebo (n = 20) | |
|---|---|---|---|---|---|---|
| RI, (%) | PreTT | Post TT | PreTT | Post TT | PreTT | Post TT |
| Mean | −1.73 | −4.23 $ | −3.34 | −7.23 $, # | −2.27 | −0.87 |
| SD | 0.71 | 1.26 | 1.00 | 1.88 | 1.19 | 2.36 |

$ p < 0.001 compared to baseline and placebo,
# p < 0.001 Crominex 400 mcg Vs Crominex 200 mcg
PreTT = Before treatment,
Post TT = After treatment Table 2 indicates that treatment with Crominex®3+ 200 mcg and 400 mcg showed significant reduction in RI, suggesting improvement in endothelial function.

TABLE 3

Comparison of Absolute change in RI

| Parameter | Crominex ®3+ 200 mcg (n = 20) | Crominex ®3+ 400 mcg (n = 20) | Placebo (n = 20) |
|---|---|---|---|
| RI (%) | −2.55 ± 1.77 | −3.89 ± 2.41 | +1.40 ± 2.68 | p < 0.001 compared between the three treatments.
All values expressed as Mean ± SD As shown in Table 3 and FIG. 1, the improvement in RI, a marker of endothelial function, was significant at p<0.001 with both 200 mcg and 400 mcg doses.

TABLE 4

Effect of Crominex ®3 + 200 mcg, 400 mcg and Placebo on Biomarkers of Oxidative Stress

| Parameter | Crominex ®3 + 200 mcg (n = 20) | | Crominex ®3 + 400 mcg (n = 20) | | Placebo (n = 20) | |
|---|---|---|---|---|---|---|
| | PreTT | Post TT | PreTT | Post TT | PreTT | Post TT |
| NO(μmol/L) | 29.20 ± 2.12 | 34.37 ± 2.73 $ | 29.14 ± 2.69 | 37.96 ± 2.28 $ | 32.40 ± 4.28 | 32.15 ± 3.75 |
| GSH(μmol/L) | 388.96 ± 36.85 | 441.8 ± 43.24 # | 397.49 ± 47.68 | 481.38 ± 46.77 # | 414.23 ± 62.88 | 421.2 ± 64.55 |
| MDA(nmol/ml) | 3.72 ± 0.50 | 3.32 ± 0.49 ^ | 3.76 ± 0.52 | 3.08 ± 0.49 ^ | 3.72 ± 0.69 | 3.82 ± 0.61 |
| hsCRP(μg/L) | 3.14 ± 1.13 | 2.38 ± 1.08 @ | 3.16 ± 1.09 | 1.25 ± 0.53 @ | 3.56 ± 0.75 | 3.61 ± 0.65 |

Baseline values between all treatments are comparable
NO- $ p < 0.001 compared to baseline
GST- # p < 0.001 compared to baseline
MDA- ^ p < 0.001 compared to baseline
hsCRP- @ p < 0.001 compared to baseline
In placebo group non-significant for all biomarkers compared to baseline.

It can be seen from Table 4 that, treatment with Crominex®3+ 200 mcg and 400 mcg showed significant increase in NO and GSH and significant decrease in MDA and hsCRP levels, whereas no significant changes were observed in the placebo group.

TABLE 4A

Comparison of Absolute change in Biomarkers between the three treatment groups (All values expressed as Mean ± SD)

| Parameter | Crominex ®3+ 200 mcg (n = 20) | Crominex ®3+ 400 mcg (n = 20) | Placebo (n = 20) |
|---|---|---|---|
| NO (μmol/L) | 5.17 ± 1.90 | 8.82 ± 2.35 | −0.26 ± 2.70 |
| GSH (μmol/L) | 52.81 ± 34.59 | 83.39 ± 29.77 | 6.97 ± 29.64 |
| MDA (nmol/ml) | −0.40 ± 0.31 | −0.67 ± 0.34 | 0.10 ± 0.22 |
| hsCRP (Mcg/L) | −0.77 ± 0.59 | −1.91 ± 1.02 | 0.04 ± 0.20 |

NO- p < 0.001 Crominex ®3+ 200 mcg vs placebo and Crominex ®3+ 400 mcg vs placebo, p < 0.001 Crominex ®3+ 200 mcg vs 400 mcg.
GSH- p < 0.001 Crominex ®3+ 200 mcg vs placebo and Crominex ®3+ 400 mcg vs placebo, p < 0.001 Crominex ®3+ 200 mcg vs 400 mcg.
MDA-, p < 0.001 Crominex ®3+ 200 mcg vs placebo and Crominex ®3+ 400 mcg vs placebo. p < 0.05 Crominex ®3+ 200 mcg vs 400 mcg.
hsCRP- p < 0.05 Crominex ®3+ 200 mcg vs Crominex ®3+ 400 mcg and Crominex ®3+ 200 mcg vs placebo, p < 0.01 Crominex ®3+ 400 mcg vs placebo.

As shown in Table 4A, there was significant change observed in absolute change in the biomarkers of oxidative stress when compared to baseline and placebo.

TABLE 5

Mean percentage change in Biomarkers of Oxidative stress after 12 weeks treatment with Crominex ®3+ 200 mcg, 400 mcg and Placebo

| Parameter | Crominex ®3+ 200 mcg (n = 20) | Crominex ®3+ 400 mcg (n = 20) | Placebo (n = 20) |
|---|---|---|---|
| NO (μmol/L, %) | 17.86 ± 6.76 | 30.98 ± 10.53 | −0.28 ± 1.30 |
| GSH (μmol/L, %) | 13.92 ± 10.11 | 21.71 ± 8.71 | 1.87 ± 7.76 |
| MDA (nmol/ml, %) | −10.49 ± 8.69 | −17.81 ± 8.19 | 3.48 ± 6.39 |
| hsCRP (Mcg/L, %) | −24.49 ± 17.13 | −55.83 ± 20.55 | 2.05 ± 6.42 |

It can be observed from the above table that in,

NO- p < 0.001 Crominex ®3+ 200 mcg vs 400 mcg, p < 0.001 Crominex ®3+ 200 mcg vs placebo, p < 0.001 Crominex ®3+ 200 mcg vs Crominex ®3+ 400 mcg.
GSH- p < 0.05 Crominex ®3+ 200 mcg vs 400 mcg, p < 0.001 Crominex ®3+ 200 mcg vs placebo and Crominex ®3+ 400 mcg vs Placebo.
MDA- p < 0.01 Crominex ®3+ 200 mcg vs 400 mcg, p < 0.001 Crominex ®3+ 200 mcg vs placebo and Crominex ®3+ 400 mcg vs placebo.
hsCRP- p < 0.001 Crominex ®3+ 200 mcg vs 400 mcg, p < 0.001 Crominex ®3+ 200 mcg vs placebo and Crominex ®3+ 400 mcg vs placebo.

As shown in Table 5 and FIGS. 2-5, there was significant increase in mean percentage change in NO and GSH and decrease in MDA and hsCRP mean percentage change when compared between the three treatments.

TABLE 6

Effect of Crominex ®3 + 200 mcg, 400 mcg and Placebo on Lipid profile after 12 weeks of treatment

| Parameter | Crominex ®3 + 200 mcg (n = 20) | | Crominex ®3 + 400 mcg (n = 20) | | Placebo (n = 20) | |
|---|---|---|---|---|---|---|
| | PreTT | Post TT | PreTT | Post TT | PreTT | Post TT |
| Total Cholesterol (mg/dl) | 176.6 ± 21.46 | 160.3 ± 20.50 $ | 179.79 ± 20.87 | 146.7 ± 14.71 $ | 178.25 ± 17.56 | 183.50 ± 19.90 |
| HDL-C (mg/dl) | 36.45 ± 4.71 | 40.65 ± 3.99 ** | 34.05 ± 3.75 | 43.10 ± 3.82 ** | 32.70 ± 3.01 | 32.75 ± 3.24 |
| LDL-C (mg/dl) | 127.2 ± 16.86 | 106.4 ± 18.27 @ | 128.65 ± 18.63 | 92.30 ± 12.35 @ | 135.55 ± 15.88 | 140.10 ± 14.81 |
| Triglycerides (mg/dl) | 177.9 ± 21.61 | 160.0 ± 20.30 # | 183.20 ± 24.66 | 136.50 ± 21.46 # | 183.60 ± 19.30 | 184.50 ± 20.70 |
| VLDL-C (mg/dl) | 29.25 ± 3.13 | 25.3 ± 2.49 ^ | 30.15 ± 4.51 | 23.30 ± 3.23 ^ | 29.70 ± 3.83 | 30.05 ± 4.85 |

Baseline values between all treatments are comparable
TC - $ p < 0.001 compared to baseline.
HDL-C- ** p < 0.001 compared to baseline
LDL-C- @ p < 0.001 compared to baseline
TG - # p < 0.001 compared to baseline
VLDL-C- ^ p < 0.0001 compared to baseline As shown in Table 6, treatment with Crominex®3+ 200 mcg and 400 mcg showed significant reduction in TC, LDL-C, TG, VLDL-C plasma levels, and increase in HDL-C compared to baseline. In placebo group no significant changes were found in all parameters compared to baseline.

TABLE 6A

Comparison of Absolute change in Lipid profile between the three treatments (All values expressed as Mean ± SD)

| Parameter | Crominex ®3+ 200 mcg (n = 20) | Crominex ®3+ 400 mcg (n = 20) | Placebo (n = 20) |
|---|---|---|---|
| Total Cholesterol (mg/dl) | −16.3 ± 6.47 | −33.15 ± 14.99 | 5.25 ± 8.53 |
| HDL-C (mg/dl) | 4.20 ± 1.70 | 9.05 ± 3.50 | 0.05 ± 2.28 |
| LDL-C (mg/dl) | −20.06 ± 9.28 | −36.35 ± 13.25 | 4.55 ± 6.34 |
| Triglycerides (mg/dl) | −17.90 ± 6.62 | −46.70 ± 16.84 | 0.90 ± 6.67 |
| VLDL-C (mg/dl) | −3.95 ± 1.76 | −4.80 ± 6.03 | 0.35 ± 2.56 |

TC-, $p < 0.001$ Crominex ®3+ 200 mcg vs 400 mcg, $p < 0.001$ Crominex ®3+ 200 mcg vs placebo and Crominex ®3+ 400 mcg vs Placebo
HDL- $p < 0.001$ Crominex ®3+ 200 mcg vs Crominex ®3+ 400 mcg, $p < 0.001$ Crominex ®3+ 200 mcg vs placebo and Crominex ®3+ 400 mcg vs Placebo
LDL-C - $p < 0.001$ Crominex ®3+ 200 mcg vs 400 mcg, $p < 0.001$ Crominex ®3+ 200 mcg vs Placebo and Crominex ®3+ 400 mcg vs Placebo.
TG - $p < 0.001$ Crominex ®3+ 200 mcg vs Crominex ®3+ 400 mcg, $p < 0.001$ Crominex ®3+ 200 mcg vs placebo and Crominex ®3+ 400 mcg vs Placebo
VLDL-C- $p < 0.001$ Crominex ®3+ 200 mcg vs 400 mcg, $p < 0.001$ Crominex ®3+ 200 mcg vs Placebo and Crominex ®3+ 400 mcg vs Placebo The above Table 6A indicates that, there was significant difference observed in absolute change in lipid parameters when compared among the three treatments.

TABLE 6B

Mean percentage change in Lipid profile after 12 weeks of treatment with Crominex ®3+ 200 mcg, Crominex ®3+ 400 mcg and Placebo

| Parameter | Crominex ®3+ 200 mcg (n = 20) | Crominex ®3+ 400 mcg (n = 20) | Placebo (n = 20) |
|---|---|---|---|
| Total Cholesterol (mg/dl, %) | −9.25 ± 3.48 | −18.05 ± 6.86 | 2.95 ± 4.81 |
| HDL-C (mg/dl, %) | 12.03 ± 5.90 | 27.34 ± 11.74 | 0.32 ± 6.99 |
| LDL-C (mg/dl, %) | −16.37 ± 7.47 | −27.70 ± 7.85 | 3.59 ± 4.91 |
| Triglycerides (mg/dl, %) | −10.07 ± 3.37 | −25.41 ± 8.16 | 0.48 ± 3.60 |
| VLDL-C (mg/dl, %) | −13.3 ± 5.14 | −22.42 ± 6.02 | 1.04 ± 8.71 |

TC- $p < 0.001$ Crominex ®3+ 200 mcg vs Crominex ®3+ 400 mcg, Crominex ®3+ 200 mcg vs placebo and Crominex ®3+ 400 mcg vs placebo
HDL-C- $p < 0.001$ Crominex ®3+ 200 mcg vs Crominex ®3+ 400 mcg, $p < 0.001$ between Crominex ®3+ 400 mcg vs placebo and Crominex ®3+ 200 mcg vs Placebo
LDL- $p < 0.001$ Crominex ®3+ 200 mcg vs Crominex ®3+ 400 mcg, $p < 0.001$ between Crominex ®3+ 200 mcg vs placebo, $p < 0.001$ TC 400 mcg Vs placebo
TG - $p < 0.001$ Crominex ®3+ 200 mcg Vs Crominex ®3+ 400 mcg, $p < 0.001$ Crominex ®3+ 200 mcg Vs placebo and Crominex ®3+ 400 mcg Vs placebo
VLDL- $p < 0.001$ Crominex ®3+ 200 mcg Vs Crominex ®3+ 400 mcg, $p < 0.001$ Crominex ®3+ 200 mcg Vs Placebo and Crominex ®3+ 400 mcg vs placebo As shown in Table 7, treatment with Crominex®3+ 200 mcg and Crominex®3+ 400 mcg showed significant reduction in HbA1c levels compared to baseline.

TABLE 7A

Comparison of absolute change between the three treatments on Glycosylated Hemoglobin A1c (HbA1c %)

| Parameter | Crominex ®3+ 200 mcg (n = 20) | Crominex ®3+ 400 mcg (n = 20) | Placebo (n = 20) |
|---|---|---|---|
| HbA1c (%) | −0.13 ± 0.21# | −0.52 ± 0.20$ | 0.06 ± 0.18 |

= $p < 0.01$ Crominex ®3+ 200 Vs Placebo, $p < 0.001$ Crominex ®3+ 400 Vs Crominex ®3+ 200 and Crominex ®3+ 400 Vs Placebo As shown in Table 7A there was significant difference observed in absolute change when compared among the three treatments.

As shown in the above Tables, the present study treatment with Crominex®3+ 200 mcg and 400 mcg produced significant improvement in mean RI index compared to baseline and placebo (see FIG. 1). Elevation of (NO, GSH), and/or reduction in (MDA, hs-CRP), the levels of markers of oxidative stress were observed suggesting improvement in endothelial function in type 2 diabetic patients (FIGS. 2, 3, 4 and 5). Both the active treatments showed significant improvement in all lipid parameters (FIGS. 6, 7, 8, 9 and 10). Treatment with Crominex®3+ 200 mcg and Crominex®3+ 400 mcg significantly reduced glycosylated hemoglobin A1c levels (Table 7A) compared to baseline and placebo. All the treatments were well tolerated and no patient discontinued the study because of side effects. However it was observed that compared to Crominex®3+ 200 mcg once daily dose, Crominex®3+ 400 mcg once daily produced more pronounced responses on pharmacodynamic parameters of endothelial function and biomarkers of oxidative stress as evidenced by a significant reduction in mean RI index and significant improvement in nitric oxide, Glutathione, and hsCRP. These findings suggest that Crominex®3+ in the dose of 400 mcg once daily may be more beneficial than 200 mcg once daily dose.

Example 2: Clinical Study on Crominex® 3+ in Metabolic Syndrome Subjects

Study Design.

Patients included in the study, were of either gender, aged 30-68 years, having endothelial dysfunction defined as ≤6% change in reflection index (RI) on post salbutamol challenge test and central obesity as defined by The International Diabetes Federation guidelines, dated 2006, and any two of the following conditions:

TABLE NO 7

Effect of treatments on Glycosylated Hemoglobin A1c (HbA1c %)

| Parameter | Crominex ®3 + 200 mcg (n = 20) | | Crominex ®3 + 400 mcg (n = 20) | | Placebo (n = 20) | |
|---|---|---|---|---|---|---|
| | Pretreatment | Post treatment | Pretreatment | Post treatment | Pretreatment | Post treatment |
| HbA1c (%) | 7.14 ± 0.29 | 7.01 ± 0.36 $ | 7.24 ± 0.29 | 6.72 ± 0.36 # | 7.10 ± 0.30 | 7.16 ± 0.32 |

Baseline values between the three treatments were comparable
$ = $p < 0.05$ compared to baseline,
# = $p < 0.001$ compared to baseline (1) Raised triglycerides >150 mg/dL (1.7 mmol/L) or specific treatment for this lipid abnormality;

(2) Reduced HDL cholesterol: <40 mg/dL (1.03 mmol/L) in males, <50 mg/dL (1.29 mmol/L) in females, or specific treatment for this lipid abnormality;

(3) Raised blood pressure: systolic BP>130 or diastolic BP>85 mmHg, or treatment of previously diagnosed hypertension; and (4) Raised fasting plasma glucose of ≥100 mg/dL, previously diagnosed type 2 diabetes. If FPG is >5.6 mmol/L or 100 mg/dL, an oral glucose tolerance test is strongly recommended, but it is not necessary to define presence of syndrome.

If BM1 is >30 kg/m$^2$, central obesity can be assumed and waist circumference does not need to be measured.

Patients with severe uncontrolled hyperglyceamia, uncontrolled hypertension, cardiac arrhythmia, impaired hepatic or renal function, history of malignancy or stroke, smoking, chronic alcoholism, any other serious disease requiring active treatment and treatment with any other herbal supplements, were excluded from the study.

After screening, all the eligible subjects were randomized to receive either one of the three treatments orally for duration of 12 weeks: group 1—one capsule of Crominex®3+ 200 mcg once daily; group 2—one capsule 400 mcg once daily; group 3—one capsule of Placebo once daily.

Subjects were reviewed for follow up at 4 weeks, 8 and 12 weeks of therapy. At each visit they were evaluated for efficacy and safety. Pharmacodynamic evaluation for endothelial function was conducted at baseline and end of treatment. Blood samples were collected for evaluation of biomarkers before and at end of treatment. Safety lab investigations for hematological, hepatic and renal biochemical parameters were conducted before and at the end of the study and also as and when required (in case of any adverse drug reaction (ADR)). Subjects were enquired for the presence of ADR and the same was recorded in the case report form. Compliance to therapy was assessed by pill count method.

Assessment of endothelial function, biomarkers, safety parameters and primary and secondary efficacy parameters and data analysis were performed as described under the study with type 2 diabetic subjects in Example 1.

Results of Study.

Total of 75 subjects were screened and 61 eligible subjects completed the study. 20 subjects in group 1 receiving Crominex®3+ 200 mcg, 21 subjects in group 2 receiving Crominex®3+ 400 mcg, and 20 subjects in group 3 receiving Placebo completed the study.

TABLE 8

Demographic characteristics of all study groups

| Parameter | Crominex ® 3+ 200 mcg | Crominex ® 3+ 400 mcg | Placebo |
|---|---|---|---|
| Total No | 20 | 21 | 20 |
| Age in Yrs | 56.80 ± 5.67 | 54.90 ± 5.27 | 54.15 ± 6.47 |
| Gender (M/F) | 11/9 | 13/8 | 14/6 |
| Bodyweight (Kg) | 79.55 ± 7.47 | 77.95 ± 7.46 | 79.45 ± 6.81 |
| BMI (Kg/m$^2$) | 30.39 ± 3.39 | 29.67 ± 3.03 | 30.17 ± 2.44 |

Detailed demographic characteristics of the three study groups are shown in Table 8. There was no significant difference between treatment groups in baseline characteristics including age, weight, and body mass index.

TABLE 9

Effect of Crominex ® 3+ 200 mcg, Crominex ® 3+ 400 mcg and Placebo on blood pressure and fasting plasma glucose

| Parameter | Crominex ® 3+ 200 mcg (n = 20) | | Crominex ® 3+ 400 mcg (n = 21) | | Placebo (n = 20) | |
|---|---|---|---|---|---|---|
| | Pre TT | Post TT | Pre TT | Post TT | Pre TT | Post TT |
| Systolic Blood Pressure (mmHg) | 126.5 ± 11.14 | 126.4 ± 9.40 NS | 129.6 ± 11.05 | 128.1 ± 10.14 NS | 127.0 ± 10.79 | 127.3 ± 10.75 |
| Diastolic Blood Pressure (mmHg) | 80.80 ± 6.04 | 80.40 ± 4.69 NS | 82.24 ± 5.63 | 81.81 ± 5.28 NS | 81.80 ± 4.79 | 81.00 ± 5.04 |
| Fasting Plasma Glucose (mg/dL) | 104.65 ± 9.65 | 101.9 ± 9.58 NS | 104.5 ± 6.95 | 100.0 ± 8.77 NS | 99.85 ± 9.76 | 99.7 ± 9.28 |

NS—non-significant compared to baseline and placebo.

TABLE 10

Effect of Crominex ®3 + 200 mcg, 400 mcg and Placebo on RI (measure of endothelial function)

| Parameter | Crominex ®3 + 200 mcg (n = 20) | | Crominex ®3 + 400 mcg (n = 21) | | Placebo (n = 20) | |
|---|---|---|---|---|---|---|
| RI (%) | PreTT | Post TT | PreTT | Post TT | PreTT | Post TT |
| Mean | -2.61 | -3.24 NS | -2.34 | -5.46 # | -2.38 | -1.17 NS |
| SD | 1.21 | 2.12 | 1.30 | 1.15 | 1.24 | 2.37 |

NS—Non-significant compared to baseline, p < 0.001 Crominex ®3 + 200 mcg Vs Crominex ®3 + 400 mcg, p < 0.001 Crominex ®3 + 200 mcg Vs Placebo
# p < 0.001 Crominex ®3 + 400 mcg compared to baseline and placebo Table 10 above indicates that baseline RI was nonsignificant between the three treatments. Treatment with Crominex®3+ 400 mcg showed significant reduction in RI, suggesting improvement in endothelial function. No significant change was found in RI on treatment with placebo, although there was a minor apparent response with Crominex®3+ 200 mcg dose.

TABLE 10A

Comparison of Absolute change in RI

| Parameter | Crominex ®3+ 200 mcg (n = 20) | Crominex ®3+ 400 mcg (n = 21) | Placebo (n = 20) |
|---|---|---|---|
| RI (%) | −0.63 ± 1.82 | −3.12 ± 1.41 | 1.21 ± 2.57 |

Figure 11:
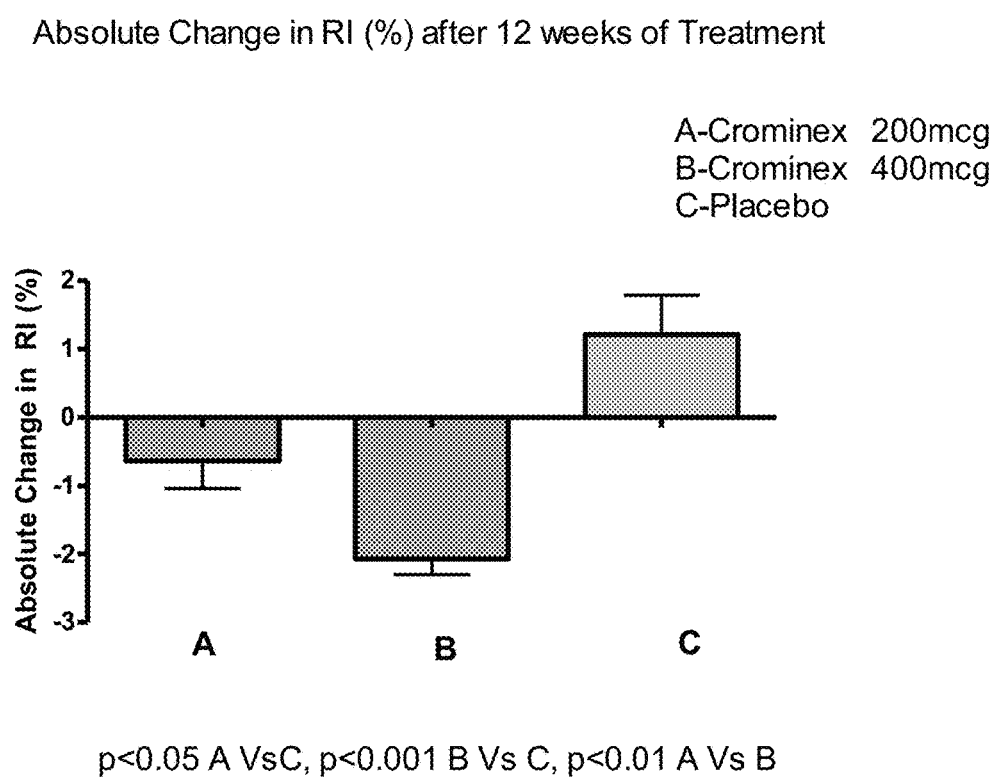
FIG. 11 illustrates absolute change in reflective index (RI %) in metabolic syndrome subjects before and after 12 weeks treatment in one embodiment in accordance with the present invention with Crominex®3+ 200 mcg and Crominex®3+ 400 mcg, as described in Table 10A.
Figure 12:
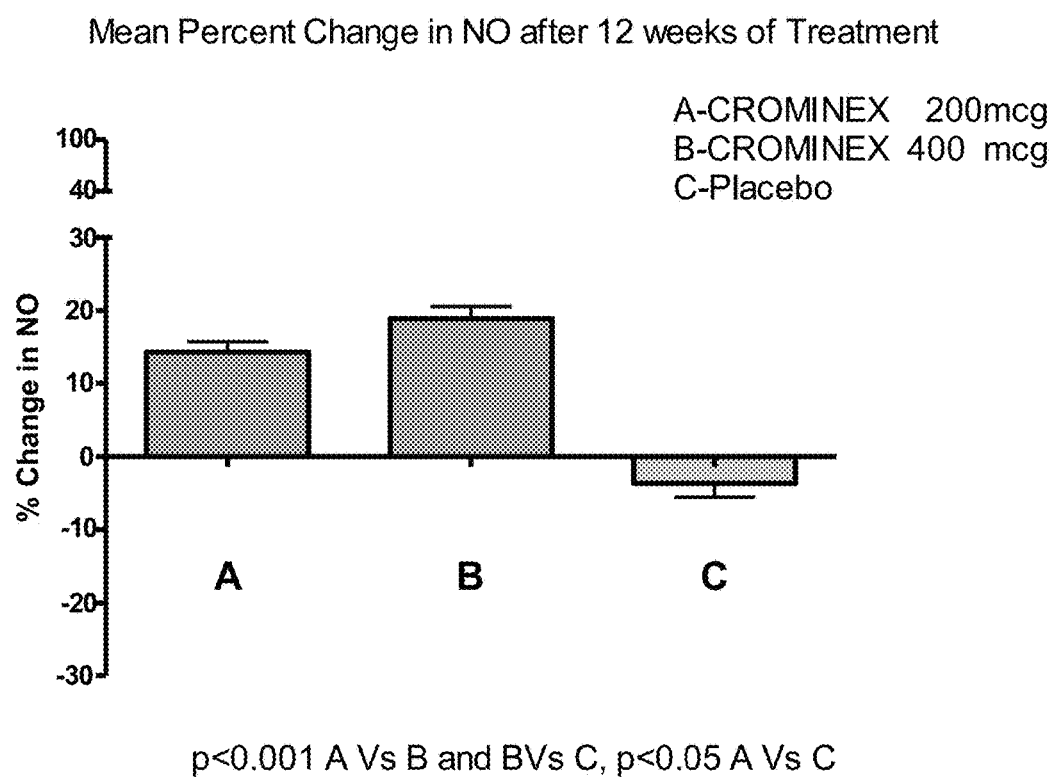
FIG. 12 illustrates mean percent change in nitric oxide (NO) concentration level in metabolic syndrome subjects before and after 12 weeks treatment in one embodiment in accordance with the present invention with Crominex®3+ 200 mcg and Crominex®3+ 400 mcg, as described in Table 11A.
Figure 13:
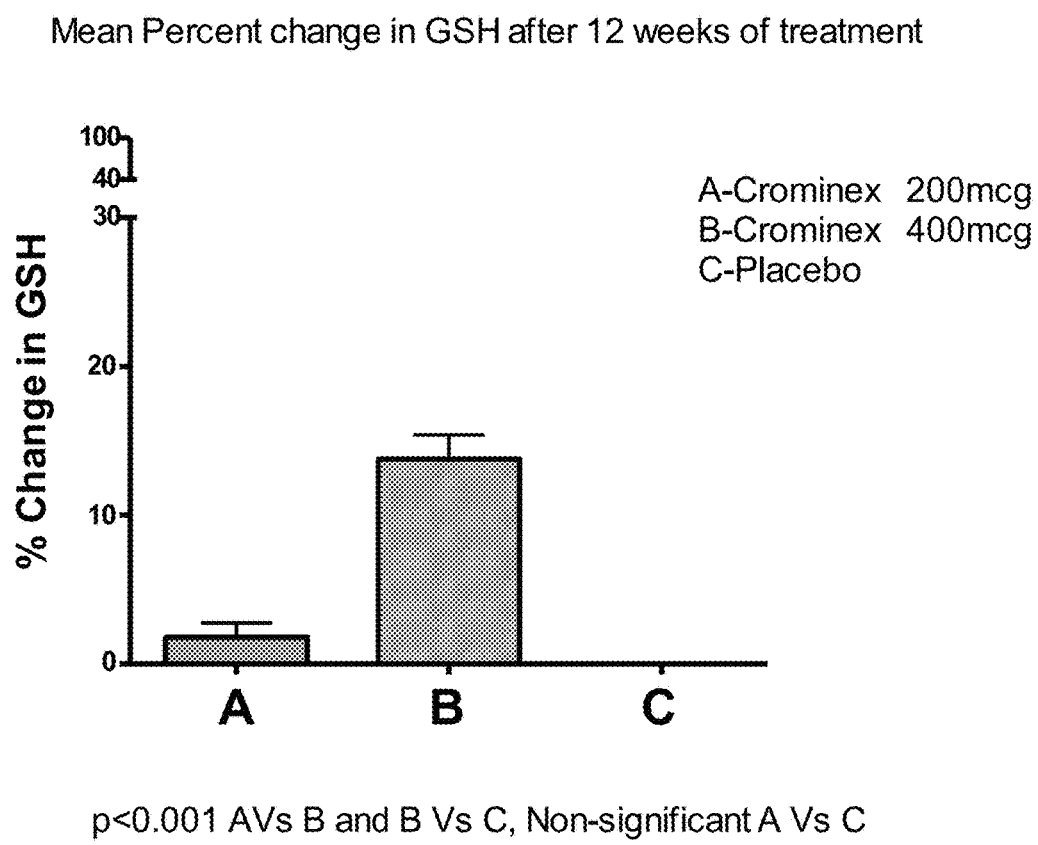
FIG. 13 illustrates mean percent change in glutathione (GSH) concentration level in metabolic syndrome subjects before and after 12 weeks treatment in one embodiment in accordance with the present invention with Crominex®3+ 200 mcg and Crominex®3+ 400 mcg, as described in Table 11A.
Figure 14:
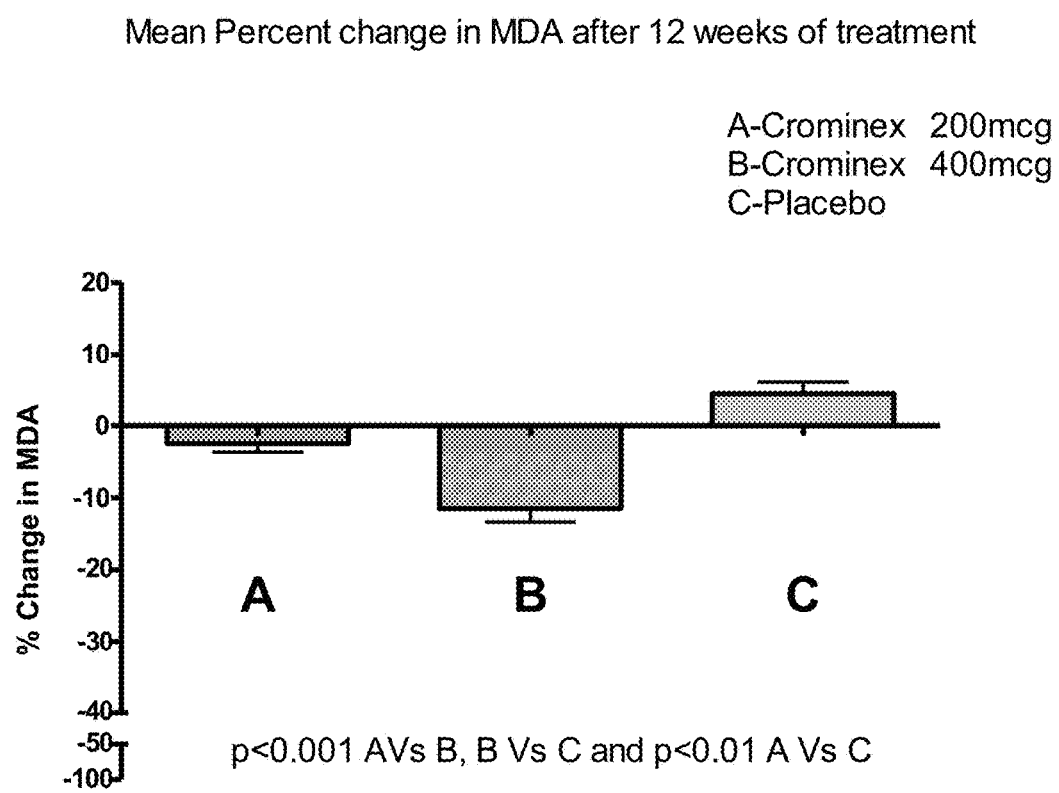
FIG. 14 illustrates mean percent change in malondialdehyde (MDA) concentration level in metabolic syndrome subjects before and after 12 weeks treatment in one embodiment in accordance with the present invention with Crominex®3+ 200 mcg and Crominex®3+ 400 mcg, as described in Table 11A.
Figure 15:
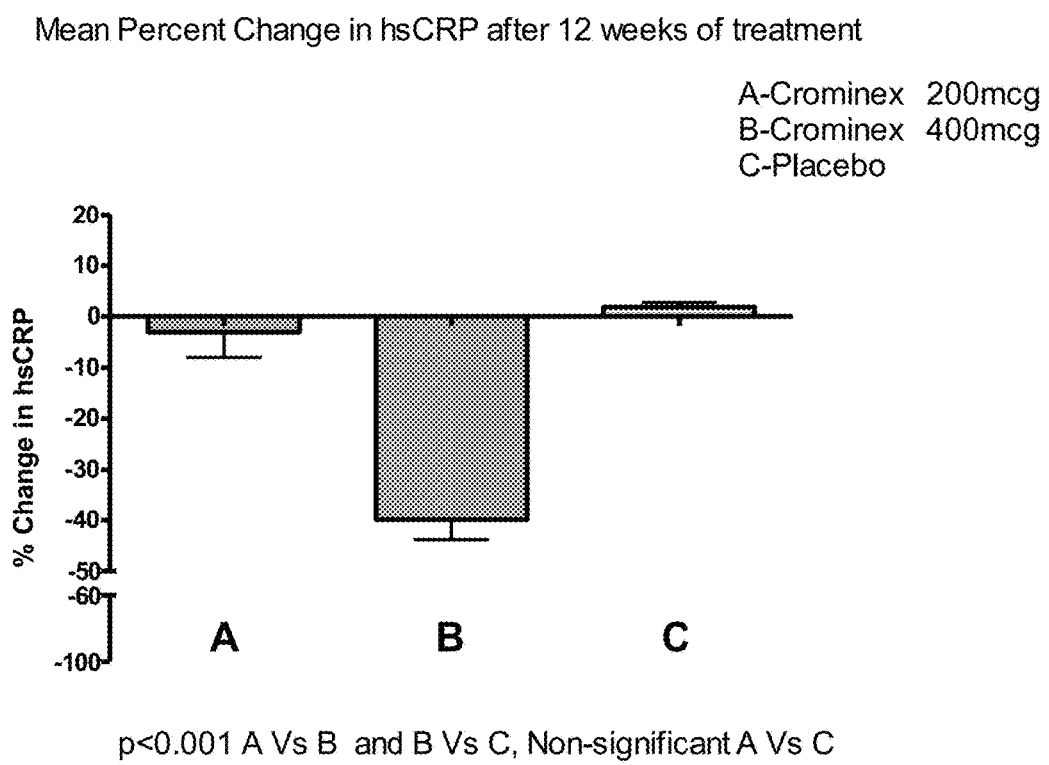
FIG. 15 illustrates mean percent change in high sensitivity C-reactive protein (hs-CRP) concentration level in metabolic syndrome subjects before and after 12 weeks treatment in one embodiment in accordance with the present invention with Crominex®3+ 200 mcg and Crominex®3+ 400 mcg, as described in Table 11A.
Figure 16:
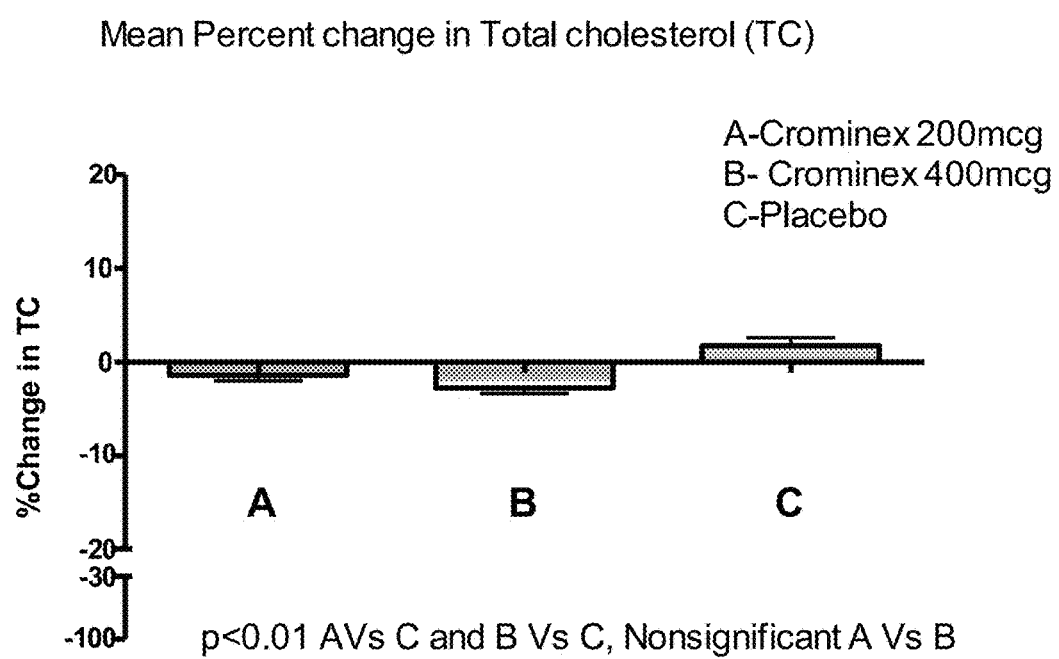
FIG. 16 illustrates mean percent change in total cholesterol (TC) concentration level in metabolic syndrome subjects before and after 12 weeks treatment in one embodiment in accordance with the present invention with the present invention with Crominex®3+ 200 mcg and Crominex®3+ 400 mcg, as described in Table 12A.
Figure 17:
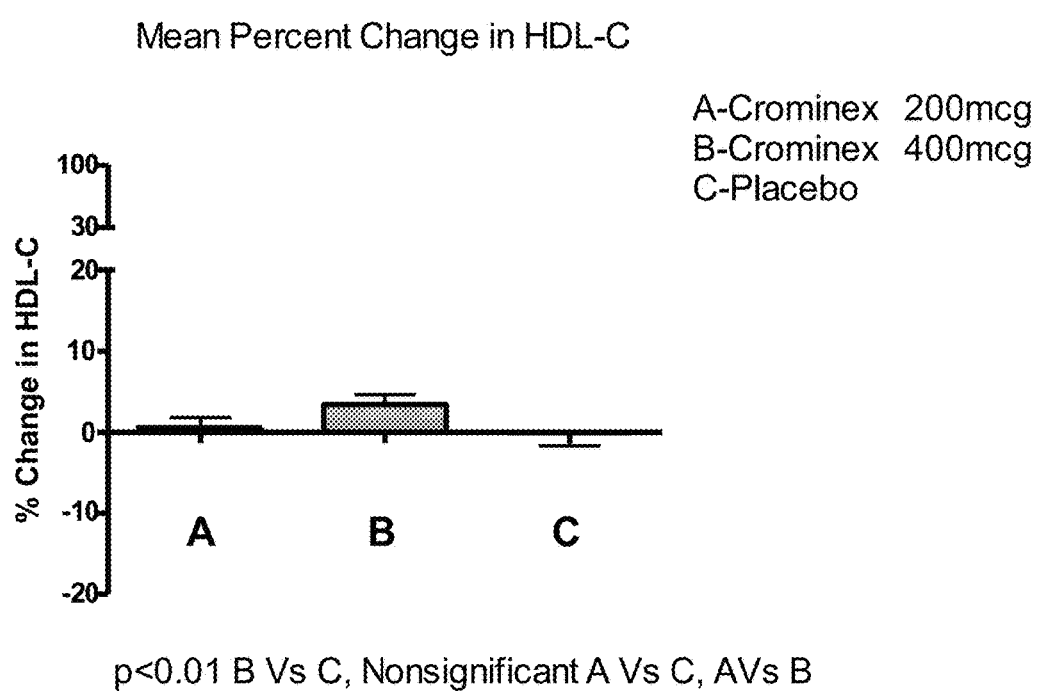
FIG. 17 illustrates mean percent change in HDL-C concentration level in metabolic syndrome subjects before and after 12 weeks treatment in one embodiment in accordance with the present invention with the present invention with Crominex®3+ 200 mcg and Crominex®3+ 400 mcg, as described in Table 12A.
Figure 18:
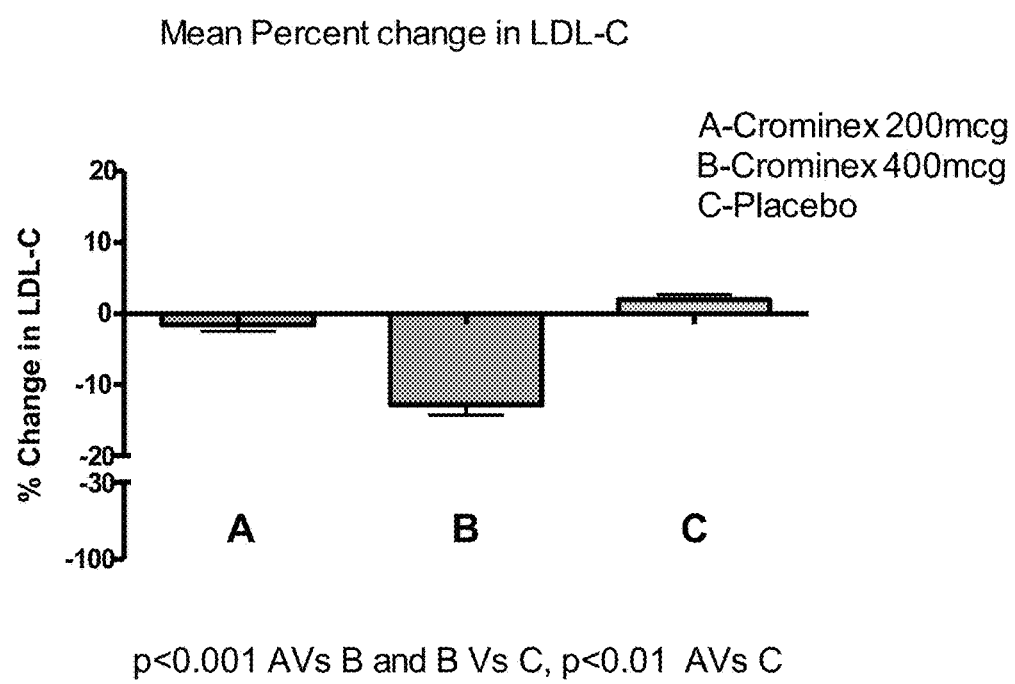
FIG. 18 illustrates mean percent change in LDL-C concentration level in metabolic syndrome subjects before and after 12 weeks treatment in one embodiment in accordance with the present invention with the present invention with Crominex®3+ 200 mcg and Crominex®3+ 400 mcg, as described in Table 12A.
Figure 19:
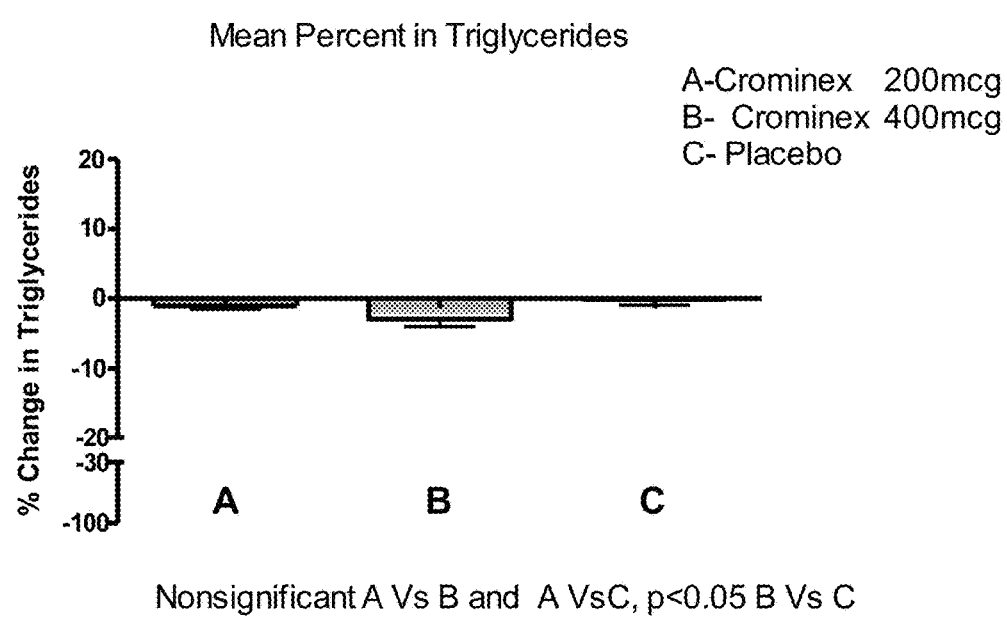
FIG. 19 illustrates mean percent change in triglycerides (TG) concentration level in metabolic syndrome subjects before and after 12 weeks treatment in one embodiment in accordance with the present invention with the present invention with Crominex®3+ 200 mcg and Crominex®3+ 400 mcg, as described in Table 12A.

$p < 0.05$ Crominex ®3+ 200 mcg Vs placebo and $p < 0.001$ Crominex ®3+ 400 mcg Vs Placebo,
$p < 0.01$ Crominex ®3+ 200 mcg Vs Crominex ®3+ 400 mcg As shown in Table 10A and FIG. 11, there was significant difference observed in the absolute change in RI, when compared among Crominex®3+ 200 mcg, Crominex®3+ 400 mcg and placebo.

TABLE 11

Effect of Crominex ®3 + 200 mcg, 400 mcg and Placebo on Biomarkers of Oxidative Stress

| | Crominex ®3 + 200 mcg (n = 20) | | Crominex ®3 + 400 mcg (n = 21) | | Placebo (n = 20) | |
|---|---|---|---|---|---|---|
| Parameter | PreTT | Post TT | PreTT | Post TT | PreTT | Post TT |
| NO(μmol/L) | 28.14 ± 2.74 | 28.60 ± 2.29 NS | 28.45 ± 2.64 | 33.79 ± 3.39 $ | 30.03 ± 2.09 | 28.88 ± 2.78 |
| GSH(μmol/L) | 372.45 ± 34.78 | 379.0 ± 37.49 NS | 368.50 ± 38.68 | 419.60 ± 56.72 # | 369.2 ± 46.76 | 368.2 ± 48.45 |
| MDA(nmol/ml) | 3.58 ± 0.57 | 3.50 ± 0.63 NS | 3.71 ± 0.65 | 3.25 ± 0.54 ^ | 3.62 ± 0.71 | 3.74 ± 0.62 |
| hsCRP(μg/L) | 3.16 ± 0.99 | 2.98 ± 0.88 NS | 3.27 ± 0.94 | 1.89 ± 0.72@ | 3.30 ± 0.61 | 3.37 ± 0.65 |

Baseline values between all treatments are comparable
NO- NS—Nonsignificant compared to baseline, $ $p < 0.001$ compared to baseline
GSH- NS—Nonsignificant compared to baseline, # $p < 0.001$ compared to baseline
MDA- NS—Nonsignificant compared to baseline, ^ $p < 0.001$ compared to baseline
hsCRP- NS—Nonsignificant compared to baseline, @$p < 0.001$ compared to baseline
In placebo group nonsignificant for all biomarkers compared to baseline.

As shown in Table 11, treatment with Crominex®3+ 400 mcg showed significant increase in NO and GSH levels and significant decrease in MDA and hsCRP levels, whereas no significant changes were observed in Crominex®3+ 200 mcg and placebo groups.

TABLE 11A

Mean percentage change in Biomarkers of Oxidative stress after 12 weeks treatment with Crominex ®3+ 200 mcg, 400 mcg and Placebo

| Parameter | Crominex ®3+ 200 mcg (n = 20) | Crominex ®3+ 400 mcg (n = 21) | Placebo (n = 20) |
|---|---|---|---|
| NO (μmol/L, %) | 1.82 ± 3.64 | 18.92 ± 7.73 | −3.67 ± 8.37 |
| GSH (μmol/L, %) | 1.80 ± 4.28 | 13.75 ± 7.40 | −0.31 ± 1.88 |
| MDA (nmol/ml, %) | −2.46 ± 5.36 | −11.51 ± 8.49 | 4.46 ± 7.20 |
| hsCRP (Mcg/L, %) | −3.05 ± 18.61 | −39.89 ± 18.15 | 1.85 ± 4.11 |

NO- $p < 0.001$ Crominex ®3+ 200 mcg Vs 400 mcg, $p < 0.05$ Crominex ®3+ 200 mcg Vs placebo and $p < 0.001$ Crominex ®3+ 400 mcg Vs Placebo.
GSH- $p < 0.001$Crominex ®3+ 200 mcg Vs 400 mcg and Crominex ®3+ 400 mcg Vs placebo, Nonsignificant Crominex ®3+ 200 mcg Vs Placebo.
MDA- $p < 0.001$ Crominex ®3+ 200 mcg Vs 400 mcg, $p < 0.01$ Crominex ®3+ 200 mcg Vs placebo and $p < 0.001$ Crominex ®3+ 400 mcg Vs placebo.
hsCRP- $p < 0.001$ Crominex ®3+ 200 mcg Vs 400 mcg and Crominex ®3+ 400 mcg Vs placebo, Nonsignificant Crominex ®3+ 200 mcg vs placebo.

Table 11A and FIGS. 12-15 indicate that there were significant increases in mean percent NO and GSH levels and decreases in MDA and hsCRP levels when compared among the three treatments.

TABLE 12

Effect of Crominex ®3 + 200 mcg, 400 mcg and Placebo on Lipid profile

| Parameter | Crominex ®3 + 200 mcg (n = 20) | | Crominex ®3 + 400 mcg (n = 21) | | Placebo (n = 20) | |
|---|---|---|---|---|---|---|
| | PreTT | Post TT | PreTT | Post TT | PreTT | Post TT |
| Total Cholesterol (mg/dl) | 178.8 ± 16.91 | 176.3 ± 17.83 * | 183.67 ± 17.54 | 178.52 ± 16.99 # | 175.8 ± 13.97 | 178.7 ± 13.18 |
| HDL-C (mg/dl) | 34.75 ± 3.09 | 35.0 ± 4.24 NS | 33.33 ± 2.57 | 34.43 ± 2.76 * | 33.15 ± 3.67 | 32.20 ± 3.52 |
| LDL-C (mg/dl) | 110.53 ± 15.6 | 108.6 ± 15.86 NS | 109.29 ± 14.69 | 94.71 ± 10.77 * | 115.9 ± 22.89 | 118.15 ± 23.35 |
| Triglycerides (mg/dl) | 189.4 ± 27.65 | 187.6 ± 28.56 NS | 188.71 ± 21.14 | 183.2 ± 22.95 * | 189.3 ± 22.79 | 188.8 ± 21.93 |

Baseline values between all treatments are comparable
TC -* $p < 0.05$ compared to baseline, # $p < 0.001$ compared to baseline
HDL-C- NS—nonsignificant compared to baseline, * $p < 0.05$ compared to baseline
LDL-C- NS—nonsignificant compared to baseline, * $p < 0.05$ compared to baseline
TG - NS—nonsignificant compared to baseline, * $p < 0.05$ compared to baseline As shown in Table 12, treatment with 400 mcg showed significant reduction in TC, LDL-C, TG levels and an increase in HDL-C compared to baseline. In the Crominex®3+ 200 mcg group except for TC no significant improvement was observed in the lipid parameters. In the placebo group no significant changes were found in all parameters compared to baseline.

TABLE 12A

Mean percentage change in Lipid profile after 12 weeks of treatment with Crominex ®3+ 200 mcg, Crominex ®3+ 400 mcg and Placebo

| Parameter | Crominex ®3+ 200 mcg (n = 20) | Crominex ®3+ 400 mcg (n = 21) | Placebo (n = 20) |
|---|---|---|---|
| Total Cholesterol (mg/dl, %) | −1.39 ± 2.71 | −2.75 ± 2.75 | 1.76 ± 3.80 |
| HDL-C (mg/dl, %) | 0.57 ± 5.63 | 3.41 ± 5.67 | −2.62 ± 6.58 |
| LDL-C (mg/dl, %) | −1.51 ± 4.43 | −12.86 ± 6.41 | 1.98 ± 3.20 |
| Triglycerides (mg/dl, %) | −1.05 ± 2.06 | −2.92 ± 4.48 | −0.12 ± 3.44 |

TC- Non-significant Crominex ®3+ 200 mcg Vs Crominex ®3+ 400 mcg, $p < 0.01$ Crominex ®3+ 200 mcg Vs placebo and Crominex ®3+ 400 mcg Vs placebo
HDL-C- Non-significant Crominex ®3+ 200 mcg Vs Crominex ®3+ 400 mcg, Non significant Crominex ®3+ 200 mcg Vs placebo and $p < 0.01$ Crominex ®3+ 400 mcg Vs placebo
LDL- $p < 0.001$ Crominex ®3+ 200 mcg Vs Crominex ®3+ 400 mcg, $p < 0.01$ between Crominex ®3+ 200 mcg Vs placebo, $p < 0.001$ Crominex ®3+ 400 mcg Vs placebo
TG - Non-significant Crominex ®3+ 200 mcg Vs Crominex ®3+ 400 mcg and Crominex ®3+ 200 mcg Vs placebo, $p < 0.05$ Crominex ®3+ 400 mcg Vs placebo Table 12A (and FIGS. 15-19) reveals that there was significance observed in mean percent change among the three treatments.

In this study with metabolic syndrome subjects, treatment with Crominex®3+ 400 mcg produced significant improvement in RI compared to baseline (see FIG. 11). Elevation of (NO, GSH), and/or reduction in (MDA, hs-CRP), the levels of markers of oxidative stress was also observed suggesting improvement in endothelial function in these patients (FIGS. 12, 13, 14 and 15). Significant improvement in lipid parameters was also seen (FIGS. 16, 17, 18 and 19). However, it was observed that compared to Crominex®3+ 200 mcg once daily dose, Crominex®3+ 400 mcg once daily dose produced more pronounced responses on pharmacodynamic parameters of endothelial function and biomarkers of oxidative stress as evidenced by a significant reduction in mean RI index and significant improvement in nitric oxide, Glutathione and hsCRP. These findings suggest that Crominex® 3+ in the dose of 400 mcg once daily may be more beneficial than 200 mcg once daily dose.

Clinical Studies Demonstrating Synergism:

When the results with Crominex® 3+ in the above two examples were highly significant, especially with the 400 mcg once daily dose in type 2 diabetics, two more clinical studies (EXAMPLES 3 & 4) were conducted at the same institute, following the same methodology as described earlier, on the individual components of Crominex® 3+, i.e., chromium chloride and *Phyllanthus emblica*+Shilajit, and other chromium supplements available in the market, i.e., chromium picolinate, chromium polynicotinate and chromium dinicocysteinate, in type 2 diabetics as well as in subjects with metabolic syndrome symptoms.

Example 3: Clinical Study on Individual Components of Crominex® 3+ and Different Chromium Supplements in Type 2 Diabetics 96 subjects completed this study. Detailed demographic characteristics of the five study groups are shown in Table 1. There was no significant difference between treatment groups in baseline characteristics including age, weight and body mass index.

TABLE 13

Demographic characteristics of all groups

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| Number of Subjects (n) | 19 | 20 | 19 | 20 | 18 |
| Age (Yrs) | 50.84 ± 4.49 | 56.30 ± 5.66 | 51.63 ± 5.67 | 49.95 ± 4.35 | 50.72 ± 4.68 |

TABLE 13-continued

Demographic characteristics of all groups

| Parameter | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| Gender (M/F) | 10/9 | 11/9 | 11/8 | 13/7 | 11/7 |
| Body weight (Kg) | 65.81 ± 6.51 | 67.98 ± 6.17 | 65.42 ± 5.84 | 64.63 ± 6.94 | 66.12 ± 6.09 |
| BMI (Kg/m$^2$) | 25.28 ± 2.07 | 25.91 ± 2.42 | 24.52 ± 2.16 | 24.47 ± 2.75 | 25.43 ± 2.39 |

As shown in Table 14, there was no statistically significant change in either systolic or diastolic blood pressure as compared to baseline in any of the five groups.

TABLE 14

Effect of Chromium chloride 400 mcg, Phyllanthus emblica 6 mg + Shilajit 6 mg, Chromium picolinate 400 mcg, Chromium polynicotinate 400 mcg and Chromium dinicocysteinate 400 mcg on Blood pressure

| Parameter | | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|---|
| Systolic blood pressure (mmHg) | Pre Tt | 117.37 ± 2.50 | 119.7 ± 3.69 | 118.63 ± 2.75 | 125.9 ± 5.17 | 118.89 ± 3.08 |
| | Post Tt | 117.26 ± 1.52 NS | 118.8 ± 2.78 NS | 117.47 ± 2.82 NS | 124.1 ± 4.88 NS | 118.11 ± 2.11 NS |
| Diastolic blood pressure (mmHg) | Pre Tt | 77.05 ± 1.68 | 77.6 ± 1.79 | 76.95 ± 2.70 | 81.2 ± 3.07 | 77.00 ± 1.41 |
| | Post Tt | 77.16 ± 1.68 NS | 77.3 ± 1.49 NS | 76.32 ± 2.14 NS | 79.7 ± 2.85 NS | 76.78 ± 1.22 NS |

NS—non significant compared to baseline

TABLE 15

Effect of 12 week treatment with Chromium chloride 400 mcg, Phyllanthus emblica 6 mg + Shilajit 6 mg, Chromium picolinate 400 mcg, Chromium polynicotinate 400 mcg and Chromium dinicocysteinate 400 mcg on fasting blood glucose

| Parameter | | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|---|
| Fasting Plasma Glucose (mg/dL) | Pre Tt | 133.05 ± 7.95 | 120.75 ± 3.80 | 133.21 ± 8.27 | 135.45 ± 7.45 | 136.8 ± 6.99 |
| | Post Tt | 134.21 ± 9.32 NS | 117.7 ± 3.42 # | 134.84 ± 6.78 NS | 136.3 ± 7.86 NS | 132.3 ± 4.41 $ |

$p < 0.001$,
$ $p < 0.05$
NS—Not significant

As shown in Table 15, there was statistically significant change after 12 weeks of treatment in the reduction of fasting plasma glucose with Phyllanthus emblica 6 mg+Shilajit 6 mg ($p<0.001$) and with Chromium dinicocysteinate 400 mcg (E) and no significant change with Chromium chloride 400 mcg (A), Chromium picolinate 400 mcg (C) and Chromium polynicotinate 400 mcg (D).

TABLE 16

Effect of 12 week treatment with Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on Reflection index (marker of endothelial function). All values expressed as Mean ± SD.

| Parameter | | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|---|
| Reflection index (%) | Pre Tt | −3.79 ± 0.82 | −1.44 ± 0.58 | −4.68 ± 1.24 | −4.3 ± 1.2 | −4.85 ± 0.74 |
| | Post Tt | −3.22 ± 0.85 # | −5.67 ± 0.54 # | −2.46 ± 0.90 # | −3.71 ± 1.1 $ | −3.82 ± 0.74 # |

$p < 0.001$,
$ $p < 0.05$

As shown in Table 16, there was statistically significant change after 12 weeks of treatment in the reduction of reflection index in Chromium chloride 400 mcg (A) ($p<0.001$), *Phyllanthus emblica* 6 mg+Shilajit 6 mg (B) ($p<0.001$), Chromium picolinate 400 mcg (C) ($p<0.001$), Chromium polynicotinate 400 mcg (D) ($p<0.05$), Chromium dinicocysteinate 400 mcg (E) ($p<0.01$).

TABLE 17

Effect of 12 week treatment with Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on absolute change of RI
All values expressed as Mean + SD

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| RI (%) | −0.57 + 0.36 #NS | −4.23 + 0.26 # | −2.22 + 0.89 # | −1.04 + 0.39 #NS | −1.03 + 0.34 #NS |

$p < 0.001$,
NS: Not significant
$p < 0.001$ between Chromium chloride 400 mcg (A) vs *Phyllanthus emblica* 6 mg + Shilajit 6 mg (B), Chromium chloride 400 mcg (A) vs Chromium picolinate 400 mcg (C), *Phyllanthus emblica* 6 mg + Shilajit 6 mg (B) vs Chromium picolinate 400 mcg (C). *Phyllanthus emblica* 6 mg + Shilajit 6 mg (B) vs Chromium polynicotinate 400 mcg (D), Chromium picolinate 400 mcg (C) vs Chromium polynicotinate 400 mcg (D), Chromium picolinate 400 mcg (C) vs Chromium dinicocysteinate 400 mcg (E).
NS: between Chromium chloride 400 mcg (A) vs Chromium polynicotinate 400 mcg (D), Chromium chloride 400 mcg (A) vs Chromium dinicocysteinate 400 mcg (E) and Chromium polynicotinate 400 mcg (D) vs Chromium dinicocysteinate 400 mcg (E)

TABLE 18

Effect of 12 week treatment with Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on biomarkers of oxidative stress
All values expressed as Mean ± SD

| Parameter | Chromium chloride 400 mcg (A) | | *Phyllanthus emblica* 6 mg + Shilajit 6 mg (B) | |
|---|---|---|---|---|
| | Pre Tt | Post Tt | Pre Tt | Post Tt |
| NO(μM/L) | 27.74 ± 2.01 | 29.60 ± 2.65 # | 28.66 ± 2.68 | 32.79 ± 3.13 # |
| GSH(μM/L) | 505.73 ± 16.66 | 527.08 ± 16.98 # | 525.67 ± 13.81 | 572.58 ± 11.13 # |
| MDA(nmol/ml) | 3.93 ± 0.39 | 3.73 ± 0.39 # | 4.35 ± 0.28 | 3.90 ± 0.27 # |
| hsCRP(mg/L) | 2.72 ± 0.53 | 2.46 ± 0.55 # | 2.64 ± 0.49 | 2.22 ± 0.51 # |

| Parameter | Chromium picolinate 400 mcg (C) | | Chromium polynicotinate 400 mcg (D) | | Chromium dinicocysteinate 400 mcg (E) | |
|---|---|---|---|---|---|---|
| | Pre Tt | Post Tt | Pre Tt | Post Tt | Pre Tt | Post Tt |
| NO(μM/L) | 29.75 ± 2.92 | 32.96 ± 2.54 # | 30.26 ± 2.48 | 31.86 ± 2.55 # | 28.88 ± 2.72 | 30.91 ± 2.87 # |
| GSH(μM/L) | 499.99 ± 30.23 | 535.96 ± 31.89 # | 507.72 ± 31.73 | 534.54 ± 32.56 # | 532.95 ± 10.63 | 563.66 ± 11.04 # |

TABLE 18-continued

Effect of 12 week treatment with Chromium chloride 400 mcg, *Phyllanthus emblica* 6 mg +
Shilajit 6 mg, Chromium picolinate 400 mcg, Chromium polynicotinate 400 mcg and
Chromium dinicocysteinate 400 mcg on biomarkers of oxidative stress
All values expressed as Mean ± SD

| MDA(nmol/ml) | 4.02 ± 0.33 | 3.78 ± 0.34 # | 3.97 ± 0.23 | 3.75 ± 0.24 # | 3.98 ± 0.31 | 3.72 ± 0.30 # |
|---|---|---|---|---|---|---|
| hsCRP(mg/L) | 2.70 ± 0.63 | 2.22 ± 0.64 # | 2.75 ± 0.47 | 2.43 ± 0.49 # | 2.79 ± 0.53 | 2.56 ± 0.58 @ |

$p < 0.001$,
@ $p < 0.01$ compared to pre-treatment in all treatment groups.

It can be seen from the above results that, after 12 weeks of treatment with all the five treatment groups showed a statistically significant increase in NO, GSH and a statistically significant decrease in MDA and hsCRP levels compared to pre-treatment.

Tables 19a-d: Mean percentage change in Biomarkers of Oxidative stress after 12 week treatment with Chromium chloride 400 mcg, *Phyllanthus emblica* 6 mg+Shilajit 6 mg, Chromium picolinate 400 mcg, Chromium polynicotinate 400 mcg and Chromium dinicocysteinate 400 mcg. All values expressed as Mean±SD.

TABLE 19a

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| NO (µM/L) | 6.98 ± 10.15@NS | 14.48 ± 5.02NS@ | 11.09 ± 4.73@NS | 5.33 ± 2.25 #@NS | 7.08 ± 2.40@NS |

($p < 0.001$),
@$p < 0.01$,
NS: Not significant $p < 0.001$ between *Phyllanthus emblica* 6 mg + Shilajit 6 mg (B) vs Chromium polynicotinate 400 mcg (D).

$p < 0.01$ between Chromium chloride 400 mcg (A) vs *Phyllanthus emblica* 6 mg + Shilajit 6 mg (B), *Phyllanthus emblica* 6 mg + Shilajit 6 mg (B) vs Chromium dinicocysteinate 400 mcg (E) and Chromium picolinate 400 mcg (C) vs Chromium polynicotinate 400 mcg (D), P = NS between Chromium chloride 400 mcg (A) vs Chromium picolinate 400 mcg (C), *Phyllanthus emblica* 6 mg + Shilajit 6 mg (B) vs Chromium picolinate 400 mcg (C), Chromium picolinate 400 mcg (C) vs Chromium dinicocysteinate 400 mcg (E). Chromium chloride 400 mcg (A) vs Chromium polynicotinate 400 mcg (D), Chromium chloride 400 mcg (A) vs Chromium dinicocysteinate 400 mcg (E) and Chromium polynicotinate 400 mcg (D) vs Chromium dinicocysteinate 400 mcg (E)

TABLE 19b

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| GSH (µM/L) | 4.22 ± 0.64 #$NS | 8.95 ± 1.42 #NS | 7.20 ± 0.82 #@NS | 5.30 ± 1.04 #@NS | 5.77 ± 1.47 #$NS |

$p < 0.001$,
@$p < 0.01$,
$$p < 0.05$,
NS: Not significant $p < 0.001$ between Chromium chloride 400 mcg (A) vs *Phyllanthus emblica* 6 mg + Shilajit 6 mg (B), Chromium chloride 400 mcg (A) vs Chromium picolinate 400 mcg (C), *Phyllanthus emblica* 6 mg + Shilajit 6 mg (B) vs Chromium picolinate 400 mcg (C), *Phyllanthus emblica* 6 mg + Shilajit 6 mg (B) vs Chromium polynicotinate 400 mcg (D) *Phyllanthus emblica* 6 mg + Shilajit 6 mg (B) vs Chromium dinicocysteinate 400 mcg (E)

$p < 0.01$ between Chromium picolinate 400 mcg (C) vs Chromium polynicotinate 400 mcg (D)

$p < 0.05$ between Chromium chloride 400 mcg (A) vs Chromium dinicocysteinate 400 mcg (E)

p = NS between Chromium chloride 400 mcg (A) vs Chromium polynicotinate 400 mcg (D), Chromium picolinate 400 mcg (C) vs Chromium dinicocysteinate 400 mcg (E) and Chromium polynicotinate 400 mcg (D) vs Chromium dinicocysteinate 400 mcg (E)

TABLE 19c

| Parameter | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| MDA (nmol/ml) | −5.14 ± 1.92 #NS | −11.40 ± 1.68 # | −6.03 ± 1.65 #NS | −5.56 ± 1.34 #NS | −6.62 ± 1.20@NS |

P < 0.001,
@p < 0.01,
$p < 0.05,
NS: Not significant p < 0.001 between Chromium chloride 400 mcg (A) vs Phyllanthus emblica 6 mg + Shilajit 6 mg (B), Phyllanthus emblica 6 mg + Shilajit 6 mg (B) vs Chromium picolinate 400 mcg (C), Phyllanthus emblica 6 mg + Shilajit 6 mg (B) vs Chromium polynicotinate 400 mcg (D)
p < 0.01 between Phyllanthus emblica 6 mg + Shilajit 6 mg (B) vs Chromium dinicocysteinate 400 mcg (E)
p = NS Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), Chromium picolinate 400 mcg (C) vs Chromium polynicotinate 400 mcg (D), Chromium picolinate 400 mcg (C) vs Chromium dinicocysteinate 400 mcg (E) and Chromium polynicotinate 400 mcg (D) vs Chromium dinicocysteinate 400 mcg (E)

TABLE 19d

| Parameter | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| hsCRP (mg/L) | −9.92 ± 3.86 #$NS | −20.15 ± 6.56NS | −18.90 ± 7.04@$NS | −11.45 ± 12.28 #NS | −8.61 ± 12.40 #@NS |

P < 0.001,
@p < 0.01,
$p < 0.05,
NS: Not significant p < 0.001 between Chromium chloride 400 mcg (A) vs Phyllanthus emblica 6 mg + Shilajit 6 mg (B), Phyllanthus emblica 6 mg + Shilajit 6 mg (B) vs Chromium polynicotinate 400 mcg (D) and Phyllanthus emblica 6 mg + Shilajit 6 mg (B) vs Chromium dinicocysteinate 400 mcg (E)
p < 0.01 between Chromium picolinate 400 mcg (C) vs Chromium dinicocysteinate 400 mcg (E)
p < 0.05 between Chromium chloride 400 mcg (A) vs Chromium picolinate 400 mcg (C)
p = NS between Chromium chloride 400 mcg (A) vs Chromium polynicotinate 400 mcg (D), Chromium chloride 400 mcg (A) vs Chromium dinicocysteinate 400 mcg (E), Chromium picolinate 400 mcg (C) vs Chromium dinicocysteinate 400 mcg (E), Phyllanthus emblica 6 mg + Shilajit 6 mg (B) vs Chromium picolinate 400 mcg (C) and Chromium polynicotinate 400 mcg (D) vs Chromium dinicocysteinate 400 mcg (E)

TABLE 20

Effect of 12 week treatment with Chromium chloride 400 mcg, Phyllanthus emblica 6 mg + Shilajit 6 mg, Chromium picolinate 400 mcg, Chromium polynicotinate 400 mcg and Chromium dinicocysteinate 400 mcg on Lipid profile
All values expressed as Mean ± SD.

| Parameter | Chromium chloride 400 mcg (A) | | Phyllanthus emblica 6 mg + Shilajit 6 mg (B) | |
|---|---|---|---|---|
| | Pre Tt | Post Tt | Pre Tt | Post Tt |
| Total Cholesterol (mg/dl) | 185.42 ± 9.68 | 184.89 ± 9.67 NS | 185.80 ± 9.02 | 182.70 ± 9.38 # |
| HDL-C (mg/dl) | 38.89 ± 2.85 | 39.95 ± 2.72 # | 37.70 ± 4.05 | 39.00 ± 4.03 # |
| LDL-C (mg/dl) | 110.33 ± 10.74 | 108.93 ± 10.40 # | 113.51 ± 11.40 | 109.62 ± 11.76 # |
| Triglycerides (mg/dl) | 181.00 ± 7.84 | 180.11 ± 7.80 $ | 172.95 ± 10.54 | 170.40 ± 9.95 # |

| Parameter | Chromium picolinate 400 mcg (C) | | Chromium polynicotinate 400 mcg (D) | | Chromium dinicocysteinate 400 mcg (E) | |
|---|---|---|---|---|---|---|
| | Pre Tt | Post Tt | Pre Tt | Pre Tt | Post Tt | Pre Tt |
| Total Cholesterol (mg/dl) | 196.63 ± 18.07 | 194.68 ± 17.93 $ | 199.40 ± 9.25 | 198.00 ± 8.64 $ | 202.06 ± 17.48 | 201.28 ± 17.29 NS |
| HDL-C (mg/dl) | 38.74 ± 1.69 | 39.84 ± 1.12 $ | 39.15 ± 1.23 | 38.65 ± 1.42 NS | 37.39 ± 2.43 | 37.83 ± 2.90 NS |
| LDL-C (mg/dl) | 121.92 ± 18.50 | 119.07 ± 18.46 # | 123.97 ± 9.73 | 123.32 ± 8.70 NS | 130.00 ± 16.71 | 128.91 ± 16.46 $ |
| Triglycerides (mg/dl) | 179.89 ± 8.65 | 178.84 ± 8.45 $ | 181.40 ± 4.47 | 180.15 ± 3.84 @ | 173.33 ± 4.83 | 172.67 ± 3.88 NS |

(p < 0.001) - compared to pre-treatment
@ (P < 0.01) - compared to pre-treatment
$ (p < 0.05) - compared to pre-treatment
NS: not significant - compared to pre-treatment.

Tables 21a-d: Mean percentage change in Lipid profile after 12 weeks of treatment with Chromium chloride 400 mcg, *Phyllanthus emblica* 6 mg+Shilajit 6 mg, Chromium picolinate 400 mcg, Chromium polynicotinate 400 mcg and Chromium dinicocysteinate 400 mcg
(All values expressed as Mean±SD).

TABLE 21a

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| Total Cholesterol (mg/dl) | −0.28 ± 0.81 #NS | −1.68 ± 0.57 # | −0.99 ± 1.08NS | −0.68 ± 1.21$NS | −0.38 ± 0.86 #NS |

$p < 0.001$, $$p < 0.05$,

NS: Not significant $p < 0.001$ between Chromium chloride 400 mcg (A) vs *Phyllanthus emblica* 6 mg + Shilajit 6 mg (B), *Phyllanthus emblica* 6 mg + Shilajit 6 mg (B) vs Chromium dinicocysteinate 400 mcg (E)

$p < 0.05$ between *Phyllanthus emblica* 6 mg + Shilajit 6 mg (B) vs Chromium polynicotinate 400 mcg (D)

p = NS between Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), *Phyllanthus emblica* 6 mg + Shilajit 6 mg (B) vs Chromium picolinate 400 mcg (C), Chromium picolinate 400 mcg (C) vs Chromium polynicotinate 400 mcg (D), Chromium picolinate 400 mcg (C) vs Chromium dinicocysteinate 400 mcg (E) and Chromium polynicotinate 400 mcg (D) vs Chromium dinicocysteinate 400 mcg (E)

TABLE 21b

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| HDL-C (mg/dl) | 2.79 ± 2.88 @NS | 3.52 ± 2.53 @NS | 2.96 ± 3.38 @NS | −1.23 ± 3.71 @NS | 1.19 ± 4.01 NS |

@$p < 0.01$, NS: Not significant $p < 0.01$ between Chromium chloride 400 mcg (A) vs Chromium polynicotinate 400 mcg (D), *Phyllanthus emblica* 6 mg + Shilajit 6 mg (B) vs Chromium polynicotinate 400 mcg (D) and Chromium picolinate 400 mcg (C) vs Chromium polynicotinate 400 mcg (D)

p = NS between Chromium chloride 400 mcg (A) vs *Phyllanthus emblica* 6 mg + Shilajit 6 mg (B), Chromium chloride 400 mcg (A) vs Chromium picolinate 400 mcg (C), Chromium chloride 400 mcg (A) vs Chromium dinicocysteinate 400 mcg (E), *Phyllanthus emblica* 6 mg + Shilajit 6 mg (B) vs Chromium picolinate 400 mcg (C), *Phyllanthus emblica* 6 mg + Shilajit 6 mg (B) vs Chromium dinicocysteinate 400 mcg (E), Chromium picolinate 400 mcg (C) vs Chromium dinicocysteinate 400 mcg (E) and Chromium polynicotinate 400 mcg (D) vs Chromium dinicocysteinate 400 mcg (E).

TABLE 21c

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| LDL-C (mg/dl) | −1.30 ± 1.42 NS | −3.48 ± 1.31 $ @ | −2.35 ± 1.81 @NS | −0.38 ± 2.10 @NS | −0.81 ± 1.52 $NS |

@$p < 0.01$, $$p < 0.05$, NS: Not significant $p < 0.01$ between *Phyllanthus emblica* 6 mg + Shilajit 6 mg (B) vs Chromium polynicotinate 400 mcg (D) and Chromium picolinate 400 mcg (C) vs Chromium polynicotinate 400 mcg (D)

P < 0.05 between *Phyllanthus emblica* 6 mg + Shilajit 6 mg (B) vs Chromium dinicocysteinate 400 mcg (E)

p = NS between Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), *Phyllanthus emblica* 6 mg + Shilajit 6 mg (B) vs Chromium picolinate 400 mcg (C), Chromium picolinate 400 mcg (C) vs Chromium dinicocysteinate 400 mcg (E) and Chromium polynicotinate 400 mcg (D) vs Chromium dinicocysteinate 400 mcg (E).

TABLE 21d

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| Triglycerides (mg/dl) | −0.49 ± 0.93 NS | −1.46 ± 0.59 NS | −0.58 ± 1.04 NS | −0.68 ± 0.83 NS | −0.37 ± 0.92 NS |

NS: Not significant p = NS between Chromium chloride 400 mcg (A) vs *Phyllanthus emblica* 6 mg + Shilajit 6 mg (B), Chromium chloride 400 mcg (A) vs Chromium picolinate 400 mcg (C), Chromium chloride 400 mcg (A) vs Chromium dinicocysteinate 400 mcg (E), Chromium chloride 400 mcg (A) vs Chromium polynicotinate 400 mcg (D), *Phyllanthus emblica* 6 mg + Shilajit 6 mg (B) vs Chromium picolinate 400 mcg (C), *Phyllanthus emblica* 6 mg + Shilajit 6 mg (B) vs Chromium polynicotinate 400 mcg (D), *Phyllanthus emblica* 6 mg + Shilajit 6 mg (B) vs Chromium dinicocysteinate 400 mcg (E), Chromium picolinate 400 mcg (C) vs Chromium polynicotinate 400 mcg (D), Chromium picolinate 400 mcg (C) vs Chromium dinicocysteinate 400 mcg (E) and Chromium polynicotinate 400 mcg (D) vs Chromium dinicocysteinate 400 mcg (E).

TABLE 22

Effect of 12 week treatment with Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on HbA1c
All values expressed as Mean ± SD

| Parameter | | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|---|
| HbA1c (%) | Pre Tt | 6.91 ± 0.16 | 7.10 ± 0.10 | 7.05 ± 0.11 | 7.08 ± 0.08 | 7.11 ± 0.08 |
| | Post Tt | 6.89 ± 0.16 NS | 6.95 ± 0.13 # | 7.03 ± 0.15 NS | 7.09 ± 0.13 NS | 7.10 ± 0.08 NS |

$P < 0.001$,
NS—Non significant

TABLE 23

Effect of Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on Absolute change in HbA1c after 12 weeks treatment.
All values expressed as Mean ± SD

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| HbA1c (%) | −0.02 ± 0.10 #NS | −0.15 ± 0.09 # | −0.02 ± 0.08 #NS | 0.01 ± 0.10 #NS | −0.01 ± 0.07 #NS |

$p < 0.001$, NS—Non significant
$p < 0.001$ between Chromium chloride 400 mcg (A) vs *Phyllanthus emblica* 6 mg + Shilajit 6 mg (B), *Phyllanthus emblica* 6 mg + Shilajit 6 mg (B) vs Chromium picolinate 400 mcg (C), *Phyllanthus emblica* 6 mg + Shilajit 6 mg (B) vs Chromium polynicotinate 400 mcg (D) and *Phyllanthus emblica* 6 mg + Shilajit 6 mg (B) vs Chromium dinicocysteinate 400 mcg (E).
p = NS between Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), Chromium picolinate 400 mcg (C) vs Chromium polynicotinate 400 mcg (D), Chromium picolinate 400 mcg (C) vs Chromium dinicocysteinate 400 mcg (E) and Chromium polynicotinate 400 mcg (D) vs Chromium dinicocysteinate 400 mcg (E).

Summary of Results from Example 3

A total of 96 eligible subjects completed the study. The subjects were randomized into five groups as following: Group A—Chromium chloride 400 mcg (n=19), group B—*Phyllanthus emblica* 6 mg+Shilajit 6 mg (n=20), group C—Chromium picolinate 400 mcg (n=19), group D—Chromium polynicotinate 400 mcg (n=20) and group E—chromium dinicocysteinate 400 mcg (n=18).

There was statistically significant change after 12 weeks of treatment in the reduction of reflection index in Chromium chloride 400 mcg (A) ($p<0.001$), *Phyllanthus emblica* 6 mg+Shilajit 6 mg (B) ($p<0.001$), Chromium picolinate 400 mcg (C) ($p<0.001$), Chromium polynicotinate 400 mcg (D) ($p<0.05$), Chromium dinicocysteinate 400 mcg (E) ($p<0.001$) as compared to pre-treatment (baseline).

It was observed that, after post-hoc analysis, for absolute change in reflection index, $p<0.001$ between Chromium chloride 400 mcg (A) vs *Phyllanthus emblica* 6 mg+Shilajit 6 mg (B), Chromium chloride 400 mcg (A) vs Chromium picolinate 400 mcg (C), *Phyllanthus emblica* 6 mg+Shilajit 6 mg (B) vs Chromium picolinate 400 mcg (C), *Phyllanthus emblica* 6 mg+Shilajit 6 mg (B) vs Chromium polynicotinate 400 mcg (D), *Phyllanthus emblica* 6 mg+Shilajit 6 mg (B) vs Chromium dinicocysteinate 400 mcg (E), Chromium picolinate 400 mcg (C) vs Chromium polynicotinate 400 mcg (D) and Chromium picolinate 400 mcg (C) vs Chromium dinicocysteinate 400 mcg (E).

The change in reflection index was not significant between Chromium chloride 400 mcg (A) vs Chromium polynicotinate 400 mcg (D), Chromium chloride 400 mcg (A) vs Chromium dinicocysteinate 400 mcg (E) and Chromium polynicotinate 400 mcg (D) vs Chromium dinicocysteinate 400 mcg (E).

There was statistically significant increase ($p<0.001$) in NO, GSH and statistically significant decrease ($p<0.001$) in MDA and hsCRP levels after 12 weeks of treatment compared to pre-treatment in all the five treatment groups except in Chromium dinicocysteinate 400 mcg (E) for hsCRP ($p<0.01$).

It was observed that, after post-hoc analysis, for NO, $p<0.001$ between *Phyllanthus emblica* 6 mg+Shilajit 6 mg (B) vs Chromium polynicotinate 400 mcg (D). The comparison between remaining groups were either lesser statistically significant (<0.01 or <0.05) or not significant (NS).

It was observed that, after post-hoc analysis, for GSH, p value was <0.001 between Chromium chloride 400 mcg (A) vs *Phyllanthus emblica* 6 mg+Shilajit 6 mg (B), Chromium chloride 400 mcg (A) vs Chromium picolinate 400 mcg (C), *Phyllanthus emblica* 6 mg+Shilajit 6 mg (B) vs Chromium picolinate 400 mcg (C), *Phyllanthus emblica* 6 mg+Shilajit 6 mg (B) vs Chromium polynicotinate 400 mcg (D) *Phyllanthus emblica* 6 mg+Shilajit 6 mg (B) vs Chromium dinicocysteinate 400 mcg (E). The comparison between remaining groups were either lesser statistically significant (<0.01 or <0.05) or not significant (NS).

It was observed that, after post-hoc analysis, for MDA, p value was <0.001 between Chromium chloride 400 mcg (A) vs *Phyllanthus emblica* 6 mg+Shilajit 6 mg (B), *Phyllanthus emblica* 6 mg+Shilajit 6 mg (B) vs Chromium picolinate 400 mcg (C), *Phyllanthus emblica* 6 mg+Shilajit 6 mg (B) vs Chromium polynicotinate 400 mcg (D). The comparison between remaining groups was either lesser statistically significant (<0.05) or not significant (NS).

It was observed that, after post-hoc analysis, for hsCRP, p value was <0.001 between Chromium chloride 400 mcg (A) vs *Phyllanthus emblica* 6 mg+Shilajit 6 mg (B), *Phyl-

*lanthus emblica* 6 mg+Shilajit 6 mg (B) vs Chromium polynicotinate 400 mcg (D) and *Phyllanthus emblica* 6 mg+Shilajit 6 mg (B) vs Chromium dinicocysteinate 400 mcg (E). The comparison between remaining groups was either lesser statistically significant (<0.05) or not significant (NS).

There was statistically significant (p<0.001) decrease in total cholesterol levels in *Phyllanthus emblica* 6 mg+Shilajit 6 mg (B), the comparison between remaining groups was either lesser statistically significant (<0.05) or not significant (NS) after 12 weeks of treatment compared to pre-treatment values.

It was observed that, after post-hoc analysis, for total cholesterol, p value was <0.001 between Chromium chloride 400 mcg (A) vs *Phyllanthus emblica* 6 mg+Shilajit 6 mg (B), *Phyllanthus emblica* 6 mg+Shilajit 6 mg (B) vs Chromium dinicocysteinate 400 mcg (E). The comparison between remaining groups were either lesser statistically significant (<0.01 or <0.05) or not significant (NS).

There was statistically significant (p<0.05) decrease in HDL-C in Chromium chloride 400 mcg (A), the comparison between remaining groups was either lesser statistically significant (<0.05) or not significant (NS) after 12 weeks of treatment compared to pre-treatment values.

It was observed that, after post-hoc analysis, for HDL-C, p value was <0.01 between Chromium chloride 400 mcg (A) vs Chromium polynicotinate 400 mcg (D), *Phyllanthus emblica* 6 mg+Shilajit 6 mg (B) vs Chromium polynicotinate 400 mcg (D) and Chromium picolinate 400 mcg (C) vs Chromium polynicotinate 400 mcg (D). The comparison between remaining groups was either lesser statistically significant (<0.05) or not significant (NS).

There was statistically significant (p<0.001) decrease in LDL-C levels in groups Chromium chloride 400 mcg (A), *Phyllanthus emblica* 6 mg+Shilajit 6 mg (B) and Chromium picolinate 400 mcg (C) after 12 weeks of treatment compared to pre-treatment values. It was observed that, after post-hoc analysis, for total LDL-C, p<0.01 between *Phyllanthus emblica* 6 mg+Shilajit 6 mg (B) vs Chromium polynicotinate 400 mcg (D) and Chromium picolinate 400 mcg (C) vs Chromium polynicotinate 400 mcg (D) The comparison between remaining groups were either lesser statistically significant (<0.01 or <0.05) or not significant (NS). There was statistically significant (p<0.001) decrease in triglyceride levels in groups *Phyllanthus emblica* 6 mg+Shilajit 6 mg (B). The comparison between remaining groups were either lesser statistically significant (<0.01 or <0.05) or not significant (NS). It was observed that, after post-hoc analysis, for triglycerides, p value was not significant (NS) in between all the treatment groups.

Example 4: Clinical Study on Individual Components of Crominex® 3+ and Different Chromium Supplements in Metabolic Syndrome Subjects 96 eligible subjects completed this study—19 in Chromium chloride 400 mcg, 20 in *Phyllanthus emblica* 6 mg+Shilajit 6 mg, 19 in Chromium picolinate 400 mcg, 20 in Chromium polynicotinate 400 mcg and 18 in Chromium dinicocysteinate 400 mcg groups completed the study.

TABLE 24

Demographic characteristics of all study groups

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| No. of subjects | 19 | 20 | 19 | 20 | 18 |
| Age in Yrs | 49.37 ± 5.64 | 51.45 ± 3.47 | 46.79 ± 4.89 | 45.55 ± 6.10 | 45.33 ± 5.42 |
| Gender (M/F) | 10/9 | 11/9 | 11/8 | 11/9 | 12/6 |
| Bodyweight (Kg) | 85.52 ± 3.84 | 81.53 ± 5.00 | 78.88 ± 3.35 | 83.23 ± 3.54 | 85.23 ± 5.66 |
| BMI (Kg/m$^2$) | 33.83 ± 1.60 | 32.86 ± 2.01 | 31.86 ± 1.59 | 33.02 ± 1.65 | 34.09 ± 2.07 |

As shown in Table 24, there was no significant difference between treatment groups in baseline characteristics including age, weight and body mass index.

TABLE 25

Effect of Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on Blood pressure after 12 weeks of treatment

| Parameter | | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|---|
| Systolic blood pressure (mmHg) | Pre Tt | 124.7 ± 3.35 | 124.6 ± 5.59 | 123.1 ± 5.39 | 125.9 ± 5.17 | 124.8 ± 3.37 |
| | Post Tt | 122.9 ± 3.42 NS | 122.7 ± 4.46 NS | 121.5 ± 4.15 NS | 124.1 ± 4.88 NS | 122.0 ± 2.66 NS |
| Diastolic blood pressure (mmHg) | Pre Tt | 80.6 ± 2.67 | 79.4 ± 3.05 | 79.2 ± 3.58 | 81.2 ± 3.07 | 80.0 ± 2.99 |
| | Post Tt | 79.8 ± 2.66 NS | 78.6 ± 2.16 NS | 78.1 ± 2.26 NS | 79.7 ± 2.85 NS | 78.8 ± 2.67 NS |

NS—non significant compared to baseline

As shown in Table 25, there was no statistically significant change after 12 weeks of treatment, in the reduction of either systolic or diastolic components of blood pressures as compared to baseline with Chromium chloride 400 mcg (A), *Phyllanthus emblica* 6 mg+Shilajit 6 mg (B), Chromium picolinate 400 mcg (C), Chromium polynicotinate 400 mcg (D) and Chromium dinicocysteinate 400 mcg (E) respectively.

TABLE 26

Effect of Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on fasting blood glucose after 12 weeks of treatment

| Parameter | | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|---|
| Fasting Plasma Glucose | Pre Tt | 104.16 ± 14.92 | 109.60 ± 18.82 | 100.95 ± 14.05 | 100.10 ± 14.00 | 101.72 ± 21.41 |
| | Post Tt | 101.32 ± 16.51 NS | 104.90 ± 16.41 @ | 96.63 ± 13.11 @ | 95.95 ± 13.32 NS | 99.50 ± 17.60 NS |

$p < 0.01$ as compared to pre-treatment in Crominex 400 mcg (A)
@ $p < 0.05$ as compared to pre-treatment in *Phyllanthus emblica* 6 mg + Shilajit 6 mg (C) and Chromium picolinate 400 mcg (D)
NS—Not significant as compared to pre-treatment in Chromium chloride 400 mcg (B), Chromium polynicotinate 400 mcg (E), Chromium dinicocysteinate 400 mcg (F).

As shown in Table 26, there was statistically significant change after 12 weeks of treatment in the reduction of fasting plasma glucose *Phyllanthus emblica* 6 mg+Shilajit 6 mg (B) ($p<0.05$), Chromium picolinate 400 mcg (C) ($p<0.05$) and not statistically significant with Chromium chloride 400 mcg (A), Chromium polynicotinate 400 mcg (D) and Chromium dinicocysteinate 400 mcg (E).

TABLE 27

Effect of Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on RI (marker of endothelial function) after 12 weeks of treatment (Mean ± SD).

| Parameter | | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|---|
| RI, % | Pre Tt | −3.06 ± 1.98 | −3.87 ± 1.19 | −3.20- ± 1.12 | −2.39 ± 2.18 | −3.55 ± 1.09 |
| | Post Tt | −3.43 ± 1.49 NS | −7.06 ± 0.88 # | −6.45 ± 0.40 # | −3.85 ± 0.86 @ | −4.58 ± 0.89 @ |

$p < 0.001$, as compared to baseline, with *Phyllanthus emblica* 6 cmg + Shilajit 6 mg (B) and Chromium picolinate 400 mcg (C).
@ $p < 0.01$, as compared to baseline, with Chromium polynicotinate 400 mcg (D) and Chromium dinicocysteinate 400 mcg (E).
NS, as compared to baseline, in Chromium chloride 400 mcg (A).

As shown in Table 27, there was statistically significant change after 12 weeks of treatment in the reduction of reflection index with ($p<0.001$), *Phyllanthus emblica* 6 mg+Shilajit 6 mg (B) ($p<0.001$), Chromium picolinate 400 mcg (C) ($p<0.001$), Chromium polynicotinate 400 mcg (D) ($p<0.01$), Chromium dinicocysteinate 400 mcg (E) ($p<0.01$) and not statistically significant in Chromium chloride 400 mcg (A).

TABLE 28

Effect of Chromium chloride 400 mcg, *Phyllanthus emblica* 6 mg + Shilajit 6 mg, Chromium picolinate 400 mcg, Chromium polynicotinate 400 mcg and Chromium dinicocysteinate 400 mcg on absolute change in RI after 12 weeks of treatment. All values expressed as Mean ± SD

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| RI (%) | −0.10 ± 1.34 #@ | −3.19 ± 1.00 #@NS | −3.25 ± 0.98 #@NS | −1.51 ± 1.78 #@NS | −0.98 ± 0.76 #@NS |

$p < 0.001$, @$p < 0.01$, NS $p < 0.001$ between Chromium chloride 400 mcg (A) vs *Phyllanthus emblica* 6 mg + Shilajit 6 mg (B), Chromium chloride 400 mcg (A) vs Chromium picolinate 400 mcg (C), *Phyllanthus emblica* 6 mg + Shilajit 6 mg (B) vs Chromium dinicocysteinate 400 mcg (E), Chromium picolinate 400 mcg (C) vs Chromium dinicocysteinate 400 mcg (E).

$p < 0.01$ between *Phyllanthus emblica* 6 mg + Shilajit 6 mg (B) vs Chromium polynicotinate 400 mcg (D), Chromium picolinate 400 mcg (C) vs Chromium polynicotinate 400 mcg (D), Chromium chloride 400 mcg (A) vs Chromium polynicotinate 400 mcg (D), Chromium chloride 400 mcg (A) vs Chromium dinicocysteinate 400 mcg (E).

NS: betwee *Phyllanthus emblica* 6 mg + Shilajit 6 mg (B) vs Chromium picolinate 400 mcg (C), Chromium polynicotinate 400 mcg (D) vs Chromium dinicocysteinate 400 mcg (E).

TABLE 29

Effect of Chromium chloride 400 mcg, *Phyllanthus emblica* 6 mg + Shilajit
6 mg, Chromium picolinate 400 mcg, Chromium polynicotinate 400 mcg and Chromium dinicocysteinate
400 mcg on biomarkers of oxidative stress after 12 weeks of treatment.

| Parameter | Chromium chloride 400 mcg (A) | | *Phyllanthus emblica* 6 mg + Shilajit 6 mg (B) | |
|---|---|---|---|---|
| | Pre Tt | Post Tt | Pre Tt | Post Tt |
| NO(μM/L) | 29.39 ± 4.43 | 30.99 ± 4.46 # | 27.75 ± 2.89 | 32.17 ± 3.07 # |
| GSH(μM/L) | 521.35 ± 49.06 | 542.56 ± 46.51 # | 477.60 ± 51.00 | 520.72 ± 54.44 # |
| MDA(nM/ml) | 3.94 ± 0.42 | 3.76 ± 0.42 # | 3.99 ± 0.37 | 3.60 ± 0.36 # |
| hsCRP(μg/L) | 2.52 ± 0.56 | 2.25 ± 0.50 # | 2.72 ± 0.57 | 1.99 ± 0.44 # |

| Parameter | Chromium picolinate 400 mcg (C) | | Chromium polynicotinate 400 mcg (D) | | Chromium dinicocysteinate 400 mcg (E) | |
|---|---|---|---|---|---|---|
| | Pre Tt | Post Tt | Pre Tt | Post Tt | Pre Tt | Post Tt |
| NO(μM/L) | 28.94 ± 3.56 | 32.94 ± 3.79 # | 31.26 ± 4.46 | 32.93 ± 4.66 # | 30.33 ± 3.58 | 32.66 ± 3.88 # |
| GSH(μM/L) | 514.35 ± 25.09 | 550.63 ± 26.21 # | 522.92 ± 20.68 | 549.43 ± 20.18 # | 529.89 ± 33.97 | 558.38 ± 33.94 # |
| MDA(nM/ml) | 3.87 ± 0.47 | 3.60 ± 0.46 # | 4.04 ± 0.40 | 3.83 ± 0.41 # | 4.00 ± 0.42 | 3.74 ± 0.42 # |
| hsCRP(μg/L) | 2.67 ± 0.44 | 2.15 ± 0.40 # | 2.76 ± 0.58 | 2.42 ± 0.54 # | 2.58 ± 0.48 | 2.24 ± 0.49 # |

$p < 0.001$ compared to pre-treatment in all treatment groups.

It can be seen from Table 29 that, after 12 weeks of treatment, all the five treatment groups showed a statistically significant increase in NO, GSH and a statistically significant decrease in MDA and hsCRP levels compared to pre-treatment.

Tables 30a-d: Mean percentage change in Biomarkers of Oxidative stress after 12 weeks treatment with Crominex 400 mcg, Chromium chloride 400 mcg, *Phyllanthus emblica* 6 mg+Shilajit 6 mg, Chromium picolinate 400 mcg, Chromium polynicotinate 400 mcg and Chromium dinicocysteinate 400 mcg.

TABLE 30a

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| NO (μM/L) | 5.50 ± 1.73 #NS | 16.06 ± 2.19 #NS | 13.92 ± 2.65 #NS | 5.35 ± 0.96 #NS | 7.68 ± 2.25 #NS |

($p < 0.001$), NS $p < 0.001$ between Chromium chloride 400 mcg (A) vs *Phyllanthus emblica* 6 mg + Shilajit 6 mg (B), Chromium chloride 400 mcg (A) vs Chromium picolinate 400 mcg (C), *Phyllanthus emblica* 6 mg + Shilajit 6 mg (B) vs Chromium polynicotinate 400 mcg (D), *Phyllanthus emblica* 6 mg + Shilajit 6 mg (B) vs Chromium dinicocysteinate 400 mcg (E), Chromium picolinate 400 mcg (C) vs Chromium polynicotinate 400 mcg (D), Chromium picolinate 400 mcg (C) vs Chromium dinicocysteinate 400 mcg (E).

P = NS between Chromium chloride 400 mcg (A) vs Chromium polynicotinate 400 mcg (D), Chromium chloride 400 mcg (A) vs Chromium dinicocysteinate 400 mcg (E), *Phyllanthus emblica* 6 mg + Shilajit 6 mg (B) vs Chromium picolinate 400 mcg (C), Chromium polynicotinate 400 mcg (D) vs Chromium dinicocysteinate 400 mcg (E).

TABLE 30b

| Parameter | Chromium chloride 400 mcg (A) | *Phyllanthus emblica* 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| GSH (μM/L) | 4.17 ± 1.80 $NS | 9.07 ± 1.43 $NS | 7.07 ± 1.95 $NS | 5.09 ± 1.36 $NS | 5.41 ± 1.38 NS |

$$p < 0.05$, NS: Not significant $p < 0.05$ between Chromium chloride 400 mcg (A) vs *Phyllanthus emblica* 6 mg + Shilajit 6 mg (B), *Phyllanthus emblica* 6 mg + Shilajit 6 mg (B) vs Chromium picolinate 400 mcg (C), *Phyllanthus emblica* 6 mg + Shilajit 6 mg (B) vs Chromium polynicotinate 400 mcg (D).

p = NS between Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), *Phyllanthus emblica* 6 mg + Shilajit 6 mg (B) vs Chromium dinicocysteinate 400 mcg (E), Chromium picolinate 400 mcg (C) vs Chromium polynicotinate 400 mcg (D), Chromium picolinate 400 mcg (C) vs Chromium dinicocysteinate 400 mcg (E), Chromium polynicotinate 400 mcg (D) vs Chromium dinicocysteinate 400 mcg (E).

TABLE 30c

| Parameter | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| MDA (nM/ml) | −4.65 ± 1.95 #@NS | −9.90 ± 1.29 @$NS | −7.14 ± 1.70 $NS | −5.38 ± 1.31 #$NS | −6.67 ± 1.47 $NS |

@$p < 0.01$, $p < 0.05$, NS $p < 0.01$ between Chromium chloride 400 mcg (A) vs Phyllanthus emblica 6 mg + Shilajit 6 mg (B).

$p < 0.05$ between Phyllanthus emblica 6 mg + Shilajit 6 mg (B) vs Chromium polynicotinate 400 mcg (D).

p = NS between Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), Phyllanthus emblica 6 mg + Shilajit 6 mg (B) vs Chromium picolinate 400 mcg (C), Phyllanthus emblica 6 mg + Shilajit 6 mg (B) vs Chromium dinicocysteinate 400 mcg (E), Chromium picolinate 400 mcg (C) vs Chromium polynicotinate 400 mcg (D), Chromium picolinate 400 mcg (C) vs Chromium dinicocysteinate 400 mcg (E), Chromium polynicotinate 400 mcg (D) vs Chromium dinicocysteinate 400 mcg (E).

TABLE 30d

| Parameter | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| hsCRP (mcg/L) | −10.99 ± 3.29 #@NS | −27.00 ± 3.75 #NS | −19.45 ± 2.98 #@NS | −12.34 ± 2.16 #NS | −13.76 ± 4.64 #NS |

@$p < 0.05$, NS Chromium chloride 400 mcg (A) vs Phyllanthus emblica 6 mg + Shilajit 6 mg (B), Phyllanthus emblica 6 mg + Shilajit 6 mg (B) vs Chromium polynicotinate 400 mcg (D), Phyllanthus emblica 6 mg + Shilajit 6 mg (B) vs Chromium dinicocysteinate 400 mcg (E).

$p < 0.05$ between Chromium chloride 400 mcg (A) vs Chromium picolinate 400 mcg (C).

p = NS between Chromium chloride 400 mcg (A) vs Chromium polynicotinate 400 mcg (D), Chromium chloride 400 mcg (A) vs Chromium dinicocysteinate 400 mcg (E), Phyllanthus emblica 6 mg + Shilajit 6 mg (B) vs Chromium picolinate 400 mcg (C), Chromium picolinate 400 mcg (C) vs Chromium polynicotinate 400 mcg (D), Chromium picolinate 400 mcg (C) vs Chromium dinicocysteinate 400 mcg (E), Chromium polynicotinate 400 mcg (D) vs Chromium dinicocysteinate 400 mcg (E).

TABLE 31

Effect of Chromium chloride 400 mcg, Phyllanthus emblica 6 mg + Shilajit 6 mg, Chromium picolinate 400 mcg, Chromium polynicotinate 400 mcg and Chromium dinicocysteinate 400 mcg on Lipid profile after 12 weeks of treatment

| | Chromium chloride 400 mcg (A) | | Phyllanthus emblica 6 mg + Shilajit 6 mg (B) | |
|---|---|---|---|---|
| Parameter | Pre Tt | Post Tt | Pre Tt | Post Tt |
| Total Cholesterol (mg/dl) | 188.37 ± 11.78 | 189.21 ± 10.80 NS | 187.75 ± 12.77 | 184.85 ± 12.42 # |
| HDL-C (mg/dl) | 37.21 ± 5.16 | 36.79 ± 5.14 NS | 37.35 ± 4.44 | 38.15 ± 4.56@ |
| LDL-C (mg/dl) | 116.42 ± 9.75 | 117.37 ± 9.13 NS | 115.84 ± 13.88 | 112.85 ± 12.73# |
| Triglycerides (mg/dl) | 173.68 ± 9.70 | 175.26 ± 9.70# | 172.80 ± 12.59 | 169.75 ± 12.20# |

| | Chromium picolinate 400 mcg (C) | | Chromium polynicotinate 400 mcg (D) | | Chromium dinicocysteinate 400 mcg (E) | |
|---|---|---|---|---|---|---|
| Parameter | Pre Tt | Post Tt | Pre Tt | Post Tt | Pre Tt | Post Tt |
| Total Cholesterol (mg/dl) | 185.05 ± 13.03 | 182.84 ± 12.60# | 181.05 ± 13.98 | 182.75 ± 14.03# | 181.94 ± 12.10 | 184.50 ± 12.49# |
| HDL-C (mg/dl) | 37.11 ± 4.32 | 37.84 ± 4.45@ | 36.85 ± 5.48 | 36.20 ± 5.15 NS | 36.83 ± 5.22 | 36.61 ± 5.67 NS |
| LDL-C (mg/dl) | 114.13 ± 12.80 | 111.55 ± 12.58# | 109.88 ± 12.76 | 111.95 ± 12.95# | 111.22 ± 14.34 | 113.64 ± 14.96# |
| Triglycerides (mg/dl) | 169.11 ± 11.02 | 167.26 ± 10.71# | 171.60 ± 9.43 | 173.00 ± 9.33# | 169.44 ± 6.24 | 171.22 ± 6.92# |

($p < 0.001$) - compared to pre-treatment

@($p < 0.05$) - compared to pre-treatment

NS: not significant - compared to pre-treatment

Tables 32a-d: Mean percentage change in Lipid profile after 12 weeks of treatment with Chromium chloride 400 mcg, Phyllanthus emblica 6 mg+Shilajit 6 mg, Chromium picolinate 400 mcg, Chromium polynicotinate 400 mcg and Chromium dinicocysteinate 400 mcg.

TABLE 32a

| Parameter | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| Total Cholesterol (mg/dl) | 0.49 ± 1.30 NS | −1.53 ± 1.39 @$NS | −1.18 ± 0.90 @$NS | 0.95 ± 1.33 @$NS | 1.40 ± 1.03 $NS |

@$p < 0.01, $p < 0.05, NS
p < 0.01 between Phyllanthus emblica 6 mg + Shilajit 6 mg (B) vs Chromium polynicotinate 400 mcg (D).
p < 0.05 between Phyllanthus emblica 6 mg + Shilajit 6 mg (B) vs Chromium dinicocysteinate 400 mcg (E), Chromium picolinate 400 mcg (C) vs Chromium polynicotinate 400 mcg (D).
p = NS between Chromium chloride 400 mcg (A) vs Phyllanthus emblica 6 mg + Shilajit 6 mg (B), Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), Phyllanthus emblica 6 mg + Shilajit 6 mg (B) vs Chromium picolinate 400 mcg (C), Chromium picolinate 400 mcg (C) vs Chromium dinicocysteinate 400 mcg (E), Chromium polynicotinate 400 mcg (D) vs Chromium dinicocysteinate 400 mcg (E).

TABLE 32b

| Parameter | Chromium chloride 400 mcg (A) | Phyllanthus emblica 6 mg ± Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| HDL-C (mg/dl) | −1.08 ± 3.45 NS | 2.21 ± 4.04 NS | 2.10 ± 2.84 NS | −1.55 ± 4.17 NS | −0.71 ± 3.95 NS |

NS: Not significant

TABLE 32c

| Parameter | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| LDL-C (mg/dl) | 0.79 + 2.51 #NS | −2.96 + 1.96 #@$NS | −2.19 + 2.10 #$NS | 1.86 + 2.13 #@$NS | 2.11 + 2.01 #$NS |

@p < 0.01, $p < 0.05, NS: Not significant
p < 0.01 between Phyllanthus emblica 6 mg + Shilajit 6 mg (B) vs Chromium polynicotinate 400 mcg (D)
P < 0.05 between Phyllanthus emblica 6 mg + Shilajit 6 mg (B) vs Chromium dinicocysteinate 400 mcg (E), Chromium picolinate 400 mcg (C) vs Chromium polynicotinate 400 mcg (D).
p = NS between Chromium chloride 400 mcg (A) vs Phyllanthus emblica 6 mg + Shilajit 6 mg (B), Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), Phyllanthus emblica 6 mg + Shilajit 6 mg (B) vs Chromium picolinate 400 mcg (C), Chromium picolinate 400 mcg (C) vs Chromium dinicocysteinate 400 mcg (E), Chromium polynicotinate 400 mcg (D) vs Chromium dinicocysteinate 400 mcg (E).

TABLE 32d

| Parameter | Chromium chloride 400 mcg (A) | Phyllanthus emblica 6 mg + Shilajit 6 mg (B) | Chromium picolinate 400 mcg (C) | Chromium polynicotinate 400 mcg (D) | Chromium dinicocysteinate 400 mcg (E) |
|---|---|---|---|---|---|
| Triglycerides (mg/dl) | 0.92 ± 1.43 | −2.04 ± 1.37 | −1.07 ± 1.20 | 0.83 ± 1.22 | 1.04 ± 1.06 | p < 0.05 between Phyllanthus emblica 6 mg + Shilajit 6 mg (C) vs Chromium dinicocysteinate 400 mcg (E).
p = NS between Chromium chloride 400 mcg (A) vs Phyllanthus emblica 6 mg + Shilajit 6 mg (B), Chromium chloride 400 mcg (A) vs Chromium picolinate 400 mcg (C), Chromium chloride 400 mcg (A) vs Chromium polynicotinate 400 mcg (D), Chromium chloride 400 mcg (A) vs Chromium dinicocysteinate 400 mcg (E), Phyllanthus emblica 6 mg + Shilajit 6 mg (B) vs Chromium picolinate 400 mcg (C), Phyllanthus emblica 6 mg + Shilajit 6 mg (B) vs Chromium polynicotinate 400 mcg (D), Chromium picolinate 400 mcg (C) vs Chromium polynicotinate 400 mcg (D), Chromium picolinate 400 mcg (C) vs Chromium dinicocysteinate 400 mcg (E), Chromium polynicotinate 400 mcg (D) vs Chromium dinicocysteinate 400 mcg (E).

Summary of Results of Example 4

The five products tested in this study rank as follows: Phyllanthus emblica 6 mg+Shilajit 6 mg followed by Chromium picolinate, Chromium polynicotinate and Chromium dinicocysteinate, in that order. Though some of the results show statistical significance, they may not be of clinical significance.

It is important to look at overall summary of the results from all the four clinical studies in order to appreciate the efficacy and synergistic activity of Crominex®. See, Tables 33 and 34.

Overall Summary of Results from all Examples

The overall, comprehensive summary of the results from the four clinical studies are shown in Tables 33 and 34.

mcg group in Type 2 diabetics provided significantly higher results than the sum of the individual groups for nitric oxide (31.0 vs 11.1), glutathione (21.7 vs 13.2), hsCRP (−55.8 vs −30.1), total cholesterol (−18.0 vs −1.96), HDL (27.3 vs 6.31), LDL (−27.7 vs −4.78), triglycerides (−25.4 vs −1.95) and HbA1c (−0.52 vs −0.04). Please note, except for HbA1c, for all other parameters the results are presented as %, while for HbA1c, the result is presented as absolute reduction in value. Similarly, the Crominex® 400 mcg group provided

TABLE 33

Overall summary of results for Crominex ® 200 mcg, Crominex 400 mcg, Placebo, *P. emblica* 6 mg + Shilajit 6 mg, Chromium picolinate, Chromium polynicotinate and Chromium dinicocysteinate in Type 2 diabetics (DM) and metabolic syndrome subjects (MS)

| Parameter | Crominex ® 200 mcg | | Crominex ® 400 mcg | | Placebo | | Chromium chloride 400 mcg | | *P. emblica* 6 mg + Shilajit 6 mg | | Chromium picolinate 400 mcg | | Chromium poly-nicotinate 400 mcg | | Chromium dinicocys-teinate 400 mcg | |
|---|---|---|---|---|---|---|---|---|---|---|---|---|---|---|---|---|
| | DM | MS | DM | MS | DM | MS | DM | MS | DM | MS | DM | MS | DM | MS | DM | MS |
| Fasting Glucose, % | ? | ? | ? | ? | −4.3 | ? | 0.87 | −2.7 | −3.1 | −4.2 | 1.2 | −4.27 | 0.63 | −4.14 | −3.2 | −2.18 |
| RI, % | −2.55 | −0.63 | −3.89 | −3.1 | 1.4 | 1.21 | −0.57 | −0.1 | −4.2 | −3.2 | −2.2 | −3.25 | −1.04 | −1.51 | −1.03 | −0.98 |
| NO, % | 17.86 | 1.82 | 31.0 | 18.9 | −0.28 | 3.7 | 6.98 | 5.5 | 4.1 | 16.1 | 11.1 | 13.9 | 5.33 | 5.35 | 7.08 | 7.68 |
| GSH, % | 13.9 | 1.80 | 21.7 | 13.8 | 1.87 | 0.31 | 4.22 | 4.2 | 9.0 | 9.1 | 7.2 | 7.1 | 5.3 | 5.1 | 5.77 | 5.4 |
| MDA, % | −10.5 | −2.46 | −17.8 | −11.5 | 3.48 | 4.46 | −5.14 | −4.65 | −11.4 | −9.9 | −6.03 | −7.1 | −5.56 | −5.4 | −6.62 | −6.7 |
| hsCRP, % | −24.5 | −3.05 | −55.8 | −39.9 | 2.05 | 1.85 | −9.92 | −11 | −20.2 | −27 | −18.9 | −19.45 | −11.45 | −12.34 | −8.61 | −13.76 |
| TC, % | −9.3 | −1.39 | −18.0 | −2.75 | 2.95 | 1.76 | −0.28 | 0.49 | −1.68 | −1.53 | −0.99 | −1.18 | −0.68 | 0.95 | −0.38 | 1.4 |
| HDL, % | 12.0 | 0.57 | 27.3 | 3.41 | 0.32 | −2.6 | 2.79 | −1.08 | 3.52 | 2.21 | 2.96 | 2.1 | −1.23 | −1.55 | 1.19 | −0.71 |
| LDL, % | −16.4 | −1.51 | −27.7 | −12.9 | 3.59 | 2.0 | −1.3 | 0.79 | −3.48 | −2.96 | −2.35 | −2.19 | −0.38 | 1.86 | −0.81 | 2.11 |
| TG, % | −10.1 | −1.05 | −25.4 | −2.92 | 0.48 | −0.12 | −0.49 | 0.92 | −1.46 | −2.04 | −0.58 | −1.07 | −0.68 | 0.83 | −0.37 | 1.04 |
| HbA1c (Abs.) | −0.13 | ? | −0.52 | ? | 0.06 | ? | −0.02 | ? | ? | ?−0.04 | −0.02 | ? | −0.01 | ? | −0.01 | ? |
| VLDL, % | −13.3 | | −22.4 | | 1.04 | | — | — | — | — | — | — | — | — | — | — |

TABLE 34

Synergistic activity of Crominex ® in Type 2 diabetics (DM) as well as Metabolic Syndrome subjects (MS) Results from Table 33 further summarized

| Parameter | Crominex ® 400 mcg in DM | Chromium chloride + *P. emblica* 6 mg + Shilajit 6 mg in DM | Crominex ® 400 mcg in MS | Chromium chloride + *P. emblica* 6 mg + Shilajit 6 mg in MS |
|---|---|---|---|---|
| Fasting Glucose, % | ? | 2.23 | −4.3 | −6.9 |
| RI, % | −3.89 | −4.72 | −3.1 | −3.3 |
| NO, % | 31.0 | 11.1 | 18.9 | 21.6 |
| GSH, % | 21.7 | 13.2 | 13.8 | 13.3 |
| MDA, % | −17.8 | −16.4 | −11.5 | −14.55 |
| hsCRP, % | −55.8 | −30.1 | −39.9 | −38.0 |
| TC, % | −18.0 | −1.96 | −2.75 | −1.04 |
| HDL, % | 27.3 | 6.31 | 3.41 | 1.13 |
| LDL, % | −27.7 | −4.78 | −12.9 | −2.17 |
| TG, % | −25.4 | −1.95 | −2.92 | −1.12 |
| HbA1c (Abs.) | −0.52 | ? | ? | ? |

The results from Table 33 are presented in a further summarized form to show the synergistic activity of Crominex®. The sum of the results for each parameter for chromium chloride 400 mcg and and *P. emblica* 6 mg+Shilajit 6 mg arms of the studies should be about equal to the results from Crominex® 400 mcg arm, if Crominex® did not have synergistic activity. However, the data (Table 34, columns 2 and 3) clearly demonstrates that Crominex® 400 mcg group in Type 2 diabetics provided significantly higher results than the sum of the individual groups in the metabolic syndrome group as well (Table 34, columns 4 and 5), though to a much lesser degree than in Type 2 diabetics (Table 34, columns 2 and 3). Thus, Crominex® 400 mcg has significant synergistic activity in both type 2 diabetics as well as metabolic syndrome subjects, although the synergistic activity is much more significant in type 2 diabetics. Similar results would be expected with lower or higher doses of Crominex®.

The nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. In accordance with one embodiment, suitable nutraceutically acceptable carriers can include ethanol, aqueous ethanol mixtures, water, fruit and/or vegetable juices, and combinations thereof.

The pharmaceutical compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films or oral dissolvable strips can be used. Other useful delivery systems comprise oral or nasal sprays or inhalers, and the like.

For oral administration, a chromium-containing composition, or *Phyllanthus emblica* extract and/or Shilajit may be further combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

The components of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof many comprise conventional ingredients in conventional proportions, with or without additional active compounds or principles, and such unit dosage forms may contain any suitable effective amount of the active ingredient commensurate with the intended daily dosage range to be employed.

The components of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired.

The powders and tablets preferably contain from five or ten to about seventy percent of the active compound(s). Suitable carriers are magnesium carbonate, magnesium state, talc, sugar, lactose, pectin, dextrin, starch, gelatin, tragacanth, methylcellulose, sodium carboxymethlycellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges are included. Tablets, powders, capsules, pills, cachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The chemical compound according to the present invention may thus be formulated for parenteral administration (e.g. by injection, for example bolus injection or continuous infusion) and may be presented in unit dose for in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Compositions suitable for topical administration in the mouth includes lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example with a dropper, pipette or spray. The compositions may be provided in single or multi-dose form. In compositions intended for administration to the respiratory tract, including intranasal compositions, the compound will generally have a small particle size for example of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenges itself, or it can be the appropriate number of any of these in packaged form.

Tablets, capsules and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of Remington's Pharmaceutical Sciences (Mack Publishing Co., Easton, Pa.).

Solid nutritional compositions for oral administration may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including, microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearate, stearic acid, silicone fluid, talc, waxes, oils, colloidal silica, and the like. The usefulness of such excipients is well known in the art.

In one preferred embodiment, the nutritional composition may be in the form of a liquid. In accordance with this embodiment, a method of making a liquid composition is provided.

Liquid nutritional compositions for oral administration in connection with a method for preventing and/or treating inflammation, colds and/or flu can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations (RTD's) are contemplated.

Routes of Administration

The compositions may be administered by any suitable route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebal, intraocular injection or infusion) administration, or those in a form suitable for administration by inhalation or insufflations, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approx. ±10%; in other embodiments the values may range in value either above or below the stated value in a range of approx. ±5%; in other embodiments the values may range in value either above or below the stated value in a range of approx. ±2%; in other embodiments the values may range in value either above or below the stated value in a range of approx. ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A method of treating endothelial dysfunction in an individual human or animal comprising administering to the individual in need thereof an effective amount of a composition comprising trivalent chromium, an extract of *Phyllanthus emblica* and Shilajit, wherein endothelial function is improved in such a manner that the improvement made by administration of the composition is greater than the sum of the improvements made by administration of trivalent chromium alone to the individual, and administration of a combination of the extracts of *Phyllanthus emblica* and Shilajit alone to the individual, in the same doses as in the composition, separately;

wherein the composition is administered in a daily dose containing each of *Phyllanthus emblica* fruit extract and Shilajit in a range of from about 3 mg to about 7.5 mg and trivalent chromium in the range of from about 02 mg to about 0.5 mg; and wherein the improved endothelial function includes a decrease of from about 25% to about 55% in the blood level of high sensitivity C-reactive protein (hs-CRP) in the individual.

2. The method according to claim 1, wherein the extract of *Phyllanthus emblica* includes at least about 60% by weight low molecular weight hydrolyzable tannoids based on the total weight of the composition.

3. The method according to claim 1, wherein the extract of *Phyllanthus emblica* includes greater than about 70% by weight low molecular weight hydrolyzable tannoids based on the total weight of the composition.

4. The method according to claim 2, wherein the low molecular weight hydrolyzable tannoids include emblicanin-A, emblicanin-B, punigluconin, and pedunculagin.

5. The method according to claim 1, wherein the Shilajit includes at least about 50% by weight fulvic acids (FAs), at least about 10% by weight dibenzo-α-pyrone chromoproteins, and at least about 0.3% by weight total dibenzo-α-pyrones (DBPs) based on the total weight of the composition.

6. The method of claim 1, wherein the composition is prepared using spray drying or freeze drying in such a manner that exposure to heat is minimized.

7. The method of claim 1, wherein the improved endothelial function includes an increase of from about 15% to about 30% in the blood level of nitric oxide (NO) in the individual.

8. The method of claim 1, wherein the improved endothelial function includes an increase of from about 15% to about 20% in the blood level of glutathione (GSH) in the individual.

9. The method of claim 1, wherein the improved endothelial function includes a decrease of from about 10% to about 15% in the blood level of malondialdehyde (MDA) in the individual.

10. The method of claim 1, wherein the improved endothelial function includes a decrease of from about 3% to about 5% in reflective index (RI) in the individual.

11. A method of mitigating cardiovascular risk factors in an individual human or animal by improving endothelial function comprising administering to the individual in need thereof an effective amount of a composition comprising trivalent chromium, an extract of *Phyllanthus emblica* and Shilajit, wherein endothelial function is improved in such a manner that the improvement made by administration of the composition is greater than the sum of the improvements made by administration of trivalent chromium alone to the individual, and administration of a combination of the extracts of *Phyllanthus emblica* and Shilajit alone to the individual, in the same doses as in the composition, separately;

wherein the composition is administered in a daily dose containing each of *Phyllanthus emblica* fruit extract and Shilajit in a range of from about 3 mg to about 7.5 mg and trivalent chromium in the range of from about 0.2 mg to about 0.5 mg; and wherein the improved endothelial function includes a decrease of from about 25% to about 55% in the blood level of high sensitivity C-reactive protein (hs-CRP) in the individual.

12. The method according to claim 11, wherein the extract of *Phyllanthus emblica* includes at least about 60% by weight low molecular weight hydrolyzable tannoids based on the total weight of the composition.

13. The method according to claim 12, wherein the extract of *Phyllanthus emblica* includes greater than about 70% by weight low molecular weight hydrolyzable tannoids based on the total weight of the composition.

14. The method according to claim 12, wherein the low molecular weight hydrolyzable tannoids include emblicanin-A, emblicanin-B, punigluconin, and pedunculagin.

15. The method according to claim 14, wherein the Shilajit includes at least about 50% by weight fulvic acids (FAs), at least about 10% by weight dibenzo-α-pyrone chromoproteins, and at least about 0.3% by weight total dibenzo-α-pyrones (DBPs) based on the total weight of the composition.

16. The method of claim 15, wherein the composition is prepared using spray drying or freeze drying in such a manner that exposure to heat is minimized.

* * * * *

UNITED STATES PATENT AND TRADEMARK OFFICE
CERTIFICATE OF CORRECTION

PATENT NO.        : 10,183,047 B2
APPLICATION NO.   : 14/947987
DATED             : January 22, 2019
INVENTOR(S)       : Sanyasi R. Kalidindi It is certified that error appears in the above-identified patent and that said Letters Patent is hereby corrected as shown below:

In the Claims

In Column 51, Line 12, Claim 1, please delete "02" and add --0.2--.

In Column 52, Line 30, Claim 13, please delete "12" and add --11--;
Line 37, Claim 15, please delete "14" and add --11--; and
Line 43, Claim 16, please delete "15" and add --11--.

Signed and Sealed this
Twenty-seventh Day of August, 2019

Andrei Iancu
*Director of the United States Patent and Trademark Office*